US011311490B2

(12) United States Patent
Schlutermann et al.

(10) Patent No.: US 11,311,490 B2
(45) Date of Patent: Apr. 26, 2022

(54) ORAL PREPARATION WITH CONTROLLED RELEASE

(75) Inventors: Burkhard Schlutermann, Au (DE); Manfred Kohlmeyer, Basel (DE)

(73) Assignee: ADD ADVANCED DRUG DELIVERY TECHNOLOGIES LTD., Reinach (CH)

( * ) Notice: Subject to any disclaimer, the term of this patent is extended or adjusted under 35 U.S.C. 154(b) by 695 days.

(21) Appl. No.: 11/990,100

(22) PCT Filed: Aug. 10, 2005

(86) PCT No.: PCT/EP2005/008700
§ 371 (c)(1),
(2), (4) Date: Apr. 11, 2008

(87) PCT Pub. No.: WO2007/016948
PCT Pub. Date: Feb. 15, 2007

(65) Prior Publication Data
US 2010/0151017 A1 Jun. 17, 2010

(51) Int. Cl.
*A61K 9/20* (2006.01)
*A61K 9/14* (2006.01)
*A61K 9/50* (2006.01)

(52) U.S. Cl.
CPC .......... *A61K 9/5078* (2013.01); *A61K 9/2081* (2013.01); *A61K 9/5026* (2013.01)

(58) Field of Classification Search
CPC ....... A61K 9/2081; A61K 9/50; A61K 9/5026
See application file for complete search history.

(56) References Cited

U.S. PATENT DOCUMENTS

| | | | |
|---|---|---|---|
| 4,650,664 A | 3/1987 | Schepky et al. | |
| 4,803,081 A * | 2/1989 | Falk | A61K 31/44 424/488 |
| 5,376,384 A | 12/1994 | Eichel et al. | |
| 5,718,919 A | 2/1998 | Ruddy et al. | |
| 5,840,329 A * | 11/1998 | Bai | 424/458 |
| 5,869,094 A | 2/1999 | Van Egmond et al. | |
| 5,955,104 A | 9/1999 | Momberger et al. | |
| 6,962,717 B1 | 11/2005 | Huber et al. | |
| 2003/0165565 A1 | 4/2003 | Mehta | |
| 2003/0157173 A1 | 8/2003 | Percel et al. | |
| 2003/0199480 A1 * | 10/2003 | Hayes | A61K 9/2081 514/152 |
| 2005/0112115 A1 * | 5/2005 | Khan | 424/130.1 |

FOREIGN PATENT DOCUMENTS

| | | |
|---|---|---|
| DE | 102004028975 A1 * | 1/2006 ............... A61K 9/16 |
| EP | 0 249 949 | 6/1987 |
| EP | 0 472 502 | 2/1992 |
| EP | 0 609 961 A1 | 8/1994 |
| EP | 0 693 282 | 1/1996 |
| EP | 1 252 886 | 10/2002 |
| WO | WO 87/02240 | 4/1987 |
| WO | WO 95/34291 | 12/1995 |
| WO | WO 96/01621 | 1/1996 |
| WO | WO 00/06126 | 2/2000 |
| WO | WO 0006126 A1 * | 2/2000 |
| WO | WO01/15668 A1 | 8/2001 |
| WO | WO 02/09675 | 2/2002 |
| WO | WO 02/072074 | 9/2002 |
| WO | WO 03/028708 | 4/2003 |
| WO | WO 03/037248 | 5/2003 |
| WO | WO 2005/002549 | 1/2005 |

OTHER PUBLICATIONS

Nadkarni et al., J. Pharmaceutical Sciences, 1975, 64, 1554-1557.*
International Search Report dated Mar. 3, 2006.
Andreas Groebel—Inaugural Dissertation for the Acquisition of the Doctorate from the faculty of Mathematics and Natural Sciences of the Ruprecht-Karls University Heidelberg, "Production of Pellets by way of Extrusion and Spheronization Systematic Formulation Development as a Base for a Knowledge-based System", Jul. 15, 2004.
Herbert P. Fiedler "Desk Reference of Additives used in the Pharmaceutical, Cosmetics and Affiliated Industries", ISBN 3-87193-230-2 & ISBN 3-87193-234-5, vol. 1 (A-K), 5th Edition, 2002.
Red List 2000, Directory of Medications for Germany (including EU Approvals).
Kurt H. Bauer et al. Textbook Pharmaceutical Technology, Includes an introduction to Bio Pharmacy, 7th Edition, Germany, 2002.
K. Lehmann et al. "Tableting of Coated Particles", Acta Pharm. Technol., 1990, 36, 7S.
R. Chopra et al. "The influence of pellet shape and surface properties on the drug release from uncoated and coated pellets", Int. J. Pharm., 2002, 239, 171-178—D2.
R. Chopra et al. "Preparation of Pellets of Different Shape and Their Characterization", Pharm. Dev. Techn., 2001, 6, 495-503—D3.
Chopra et al. "The Influence of Film Coating on Pellet Properties", Pharm. Dev. Techn., 2002, 7, 59-68—D7.
J. Chatchawalsaisin et al. "The preparation by extrusion/spheronization and the properties of pellets containing drugs, microcrystalline cellulose and glyceryl monostearate", Eur. J. Pharm. Sci., 2005, 24, 35-48—D8.
D9: U.H. Opitz, Review "Multipartikuläre Tabletten", Pharmazeutische Wissenschaft, Jun. 2005, 136-141 D9a: Publication Information of D9—http://www.uni-duesseldorf.de/koidapharmalehrbuch/_apothekenmagazin/Fortbildungsartikel.html.

(Continued)

*Primary Examiner* — Kyle A Purdy
(74) *Attorney, Agent, or Firm* — Haug Partners LLP

(57) ABSTRACT

A pharmaceutical pellet is disclosed, comprising a spherical core containing active ingredient with a smooth surface and a coating on the core which controls the release of the active ingredient in a pH-independent manner. With such a pellet the release of the active ingredient can follow a profile with a lag phase of 60 minutes to 840 minutes, a proportion of 5 wt. % or less of the active ingredient being released during the lag phase. The active ingredient can furthermore be released from the pellet with a profile such that after the lag phase the release of the active ingredient amounts to between 3 and 25 wt. % per hour.

27 Claims, 24 Drawing Sheets

(56) References Cited

OTHER PUBLICATIONS

J.J. Torrado et al. "Effect of different excipients an the tableting of coated particles", Int. J. Pharm., 1994, 106, 149-155—D10.

J. L. Haslam et al. "Tableting of controlled release multiparticulates, the effect of millisphere size and protective overcoating", Int. J. Pharm., 1998, 173, Abstract—D12.

Wikipedia:http://en.wikipedia.org/wiki/Paracetamol, Paracetamol, p. 1-2—D13.

S.-Y. Lin et al. "Hydrophilic Excipients Modulate the Time Lag of Time-Controlled Disintegrating Pres s-coated Tablets", AAPS PharmSciTech, 2004, Article 54, p. 1-5—D 14.

Notice of opposition to European patent No. 1915137 dated May 6, 2014.

R. Chopra et al., "The influence of pellet shape and film coating on the filling of pellets into hard shell capsules", European Journal of Pharmaceutics and Biopharmaceutics 53 (2002), 327-333.

P.D. Nadkarni et al., "Effect of Surface Roughness and Coating Solvent Film Adhesion to Tablets", J. of Pharmaceutical Sciences 64 (1975),1554-1557.

J. O.-H. Sham et al., "Formulation and characterization of spray-dried powers containing nanoparticles for aerosol delivery to the lung", Int. J. of Pharmaceutics 269 (2004), 457-464.

Notice of opposition to European patent No. 1915137 dated May 7, 2014.

Euragit RL 30 D—Product Sheet: http://eudragit.evonik.com/product/eudragit/en/products-services/eudragit-products/sustained-release-formulations/rl-30-d/pages/default.aspx.

Euragit RS 30 D—Product Sheet: http://eudragit.evonik.com/product/eudragit/en/products-services/eudragit-products/sustained-release-formulations/rs-30-d/pages/default.aspx.

Brochure—Aquacoat ECD, Aqueous Coating, FMC Biopolymer—Sustained Release Moisture Barrier Taste Masking, www.fmcbiopolymer.com, www.pharm_info@fmc.com pp. 1-9; 1998.

Halder et al., *Preparation and In Vitro Evaluation of Polystyrene-Coated Diltiazem-Resin Complex by Oil-in-Water Emulsion Solvent Evaporation Method*, Published: May 26, 2006, *AAPSPharmSciTech* 2006; 7 (2) Article 46 (http://www.aapspharmscitech.org).

Definition of Surface Roughness, download from https://en.wikipedia.org/wiki/Surface_roughness, Aug. 13, 2015.

Porter and Isaac Ghebre-Sellassie, Multiparticulate Oral Drug Delivery, Section, "A. Physicochemical Properties of Core Pellets", Marcel Dekker Inc., 1994, pp. 233-239.

Pictures of Experimental pellets; D33a) smooth and round, D33b) less smooth, D33c) not smooth.

N. Sinchaipanid et al., "Influences of Layering on Theophylline Pellet Characteristics" Pharmaceutical Development and Technology, vol. 9 (2004), No. 2, pp. 163-170.

H.A. Rashid, "Centrifugal Granulating Process for Preparing Drug-Layered Pellets based on Microcrystalline Cellulose Beads", Academic Dissertation, Apr. 20, 2011, pp. 1-64 (D39a & D39b).

Michael E. Aulton et al., "Film Coat Quality", Pharmaceutical Coating Technology, edited by Graham Cole, chapter 13, pp. 363-408, Taylor & Francis Ltd. 1995.

G.R. B. Down, The Etiology of Pinhole and Bubble Defects in Enteric and Controlled-Release Film Coatings, Drug Development and Industrial Pharmacy, 17(2), 309-315 (1991).

A.M. Mehta, "Factors in the development of Oral Controlled-release Dosage Forms", Glatt®, reprinted from Pharmaceutical Manufacturing, Jan. 1986.

B.-H. Chen et al., "Finite Element Analysis of Slow Drug Release through Deformed Coating Film: Effects of Morphology and Average Thickness of Coating Film", International Journal of Pharmaceutics 234 (2002), 25-42.

C.-C. Kao et al., "Lag Time Method to Delay Drug Release to Various Sites in the Gastrointestinal Tract", Journal of Controlled Release 44 (1997), 263-270.

M. Wesseling et al., "Drug Release from Beads Coated with an Aqueous Colloidal Ethylcellulose Dispersion, Aquacoat®, or an Organic Ethylcellulose Solution", European Journal of Pharmaceutics and Biopharmaceutics 47 (1999), 33-38.

\* cited by examiner

ORAL PREPARATION WITH CONTROLLED RELEASE

FIELD OF THE INVENTION

The present invention relates to new pharmaceutical pellets, multiparticulate dosage forms based on said pellets, methods of production of pellets and methods of production of dosage forms using the pellets. The pellets and the multiparticulate dosage forms based on the pellets are characterized in particular by controlled release of the active substance.

BACKGROUND OF THE INVENTION

When medicinal products are administered orally, the active substance is released in the gastrointestinal tract, and a proportion of the active substance is absorbed. By controlling the release of the active substance it is possible to influence the extent of absorption and the duration of action. Accordingly, various proposals have been made for controlling the release of the active substance by suitable galenical formulation of the active substance.

One approach is to provide dosage forms with coatings, so that the release of the active substance can be influenced in relation to the solubility or permeability of the coatings. Said coatings can for example be applied to tablets or capsules. In this case, however, there is the disadvantage that if the coating is defective or damaged, the release of the total dose of active substance may not be controlled in the desired manner.

An alternative is offered by multiparticulate dosage forms, in which the total amount of the active substance is distributed over a larger number of smaller units, such as pellets. If the individual pellets are provided with coatings, in the case of a defective coating on one pellet only a correspondingly small proportion of the total dose of active substance is not released in the desired manner.

A further advantage of these dosage forms based on pellets is that, after ingestion, sufficiently small pellets pass relatively quickly from the stomach into the intestine. In contrast, unless they disintegrate, tablets may remain in the stomach for quite a long time, and moreover the length of time varies considerably.

Despite the known advantages of pellets or multiparticulate dosage forms it is, however, difficult to obtain a desired release behavior. This is associated with the fact that, in the state of the art, it is difficult to prepare uniformly coated pellets. Even the pellet cores that are to be coated are of inadequate quality. In particular, pellets produced by extrusion are often of nonuniform shape and moreover have a rough and uneven surface, so that subsequent coating with film becomes difficult and it is scarcely possible to obtain films of good quality.

The films or coatings employed for controlling release can have various compositions. Thus, proposals have been made for controlling release in relation to pH value, time or bacterial enzymes that are present in the intestine.

With pH-controlled systems, however, there is the problem that the release of the active substance is altered by food intake, which has an effect on the pH value in the gastrointestinal tract. Moreover, there are considerable differences regarding pH values in the gastrointestinal tract between different individuals. Variability has also been reported in the case of controlled-release dosage forms controlled enzymatically.

Certain controlled-release dosage forms are therefore not completely satisfactory. There is the further problem that it is not possible to produce desired (specified) release profiles. Furthermore, the production of controlled-release dosage forms is often difficult. There is therefore a need for new controlled-release dosage forms as well as new methods for the production of controlled-release dosage forms.

TASKS AND BRIEF DESCRIPTION OF THE INVENTION

One task of the present invention is to provide a pharmaceutical pellet for which the release of the active substance can be controlled independently of the pH value and independently of the action of enzymes.

Another task is to provide a pharmaceutical pellet for which the release of the active substance follows a profile with a lag-phase. A further task is to provide a pellet for which the release of the active substance takes place at an established rate after a lag-phase. Furthermore, according to the invention, pellet products or collections of pellets are to be provided, which comprise a multiplicity of individual pellets, each satisfying the specified requirements. Finally, according to the invention, methods are to be provided for the production of pellets, pellet products and other dosage forms.

Now, according to the invention, it was found that preparations can be provided for which the release of the active substance takes place independently of pH and independently of enzymes, if pellets are used that have a spherical core containing the active substance with a smooth surface and a coating on the core.

BRIEF DESCRIPTION OF THE FIGURES

The invention is explained in more detail below, referring to the figures.

Measurement series A relates to tablets that were produced with a compression pressure of 180 MPa and have a hardness of 80 N and a disintegration time of less than 1 minute. Measurement series B relates to tablets that were produced with a compression pressure of 240 MPa and have a hardness of 120 N and a disintegration time of less than 1 minute. Measurement series C relates to tablets that were produced with a compression pressure of 256 MPa and have a hardness of 160 N and a disintegration time of less than 1 minute.

Figure 5:
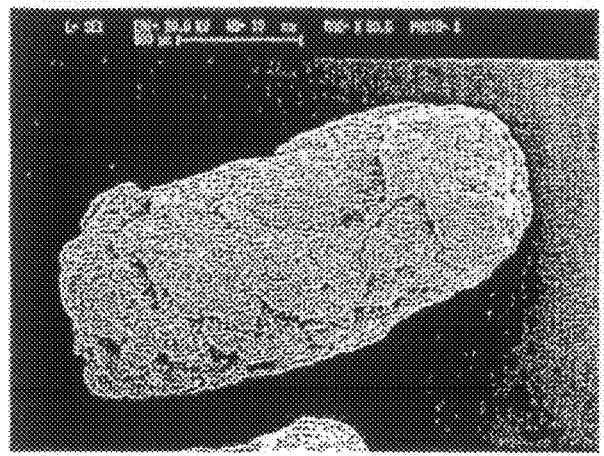

FIG. 5 shows a scanning electron micrograph (50-times magnification) of an extruded pellet with irregular shape and a rough surface.

Figure 6:
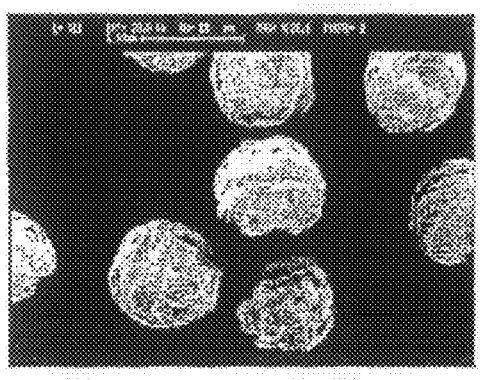
Figure 7A:
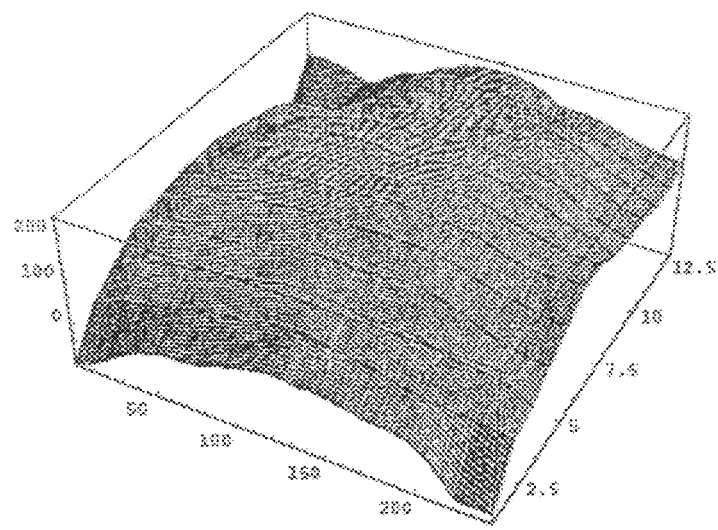
Figure 7B:
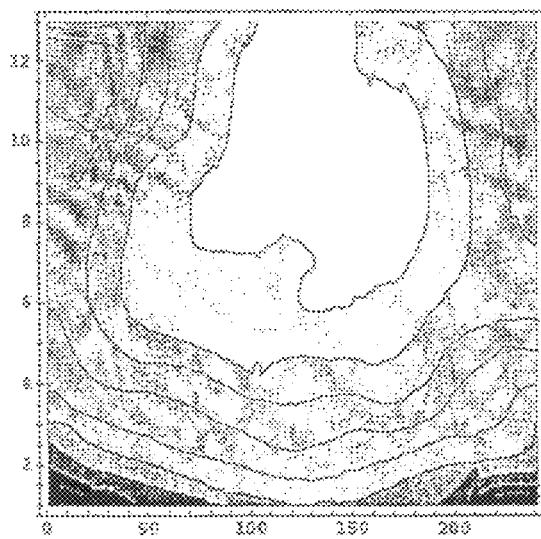
Figure 7C:
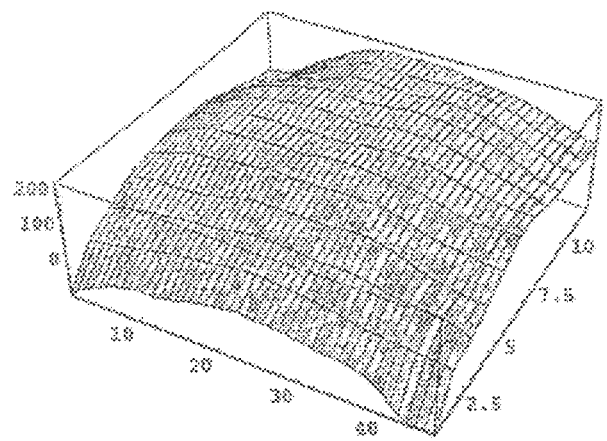
Figure 7D:
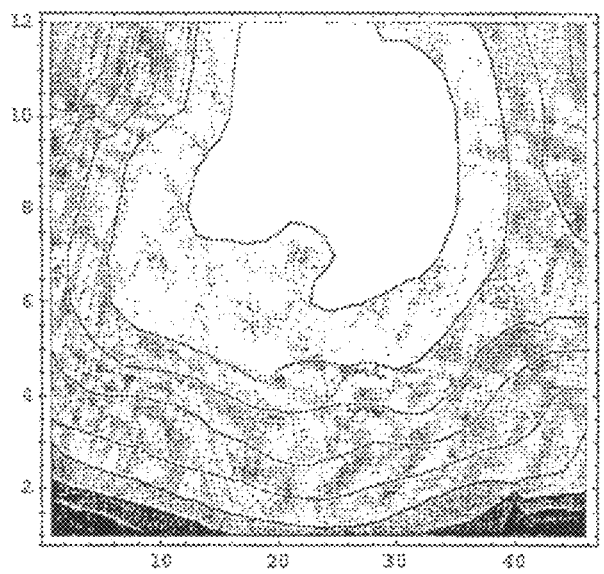
Figure 7E:
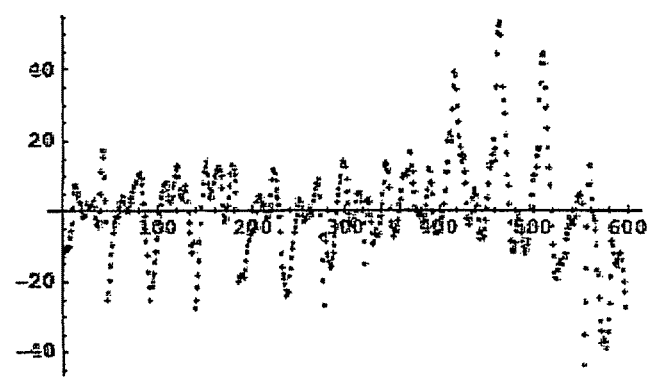
Figure 8A:
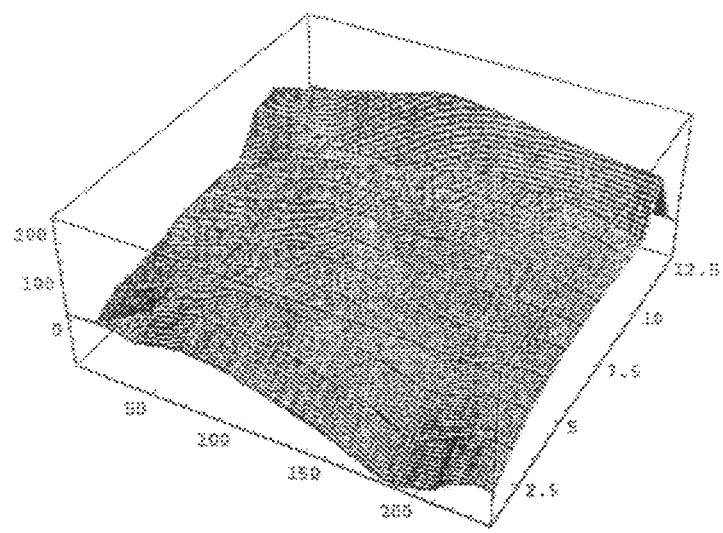
Figure 8B:
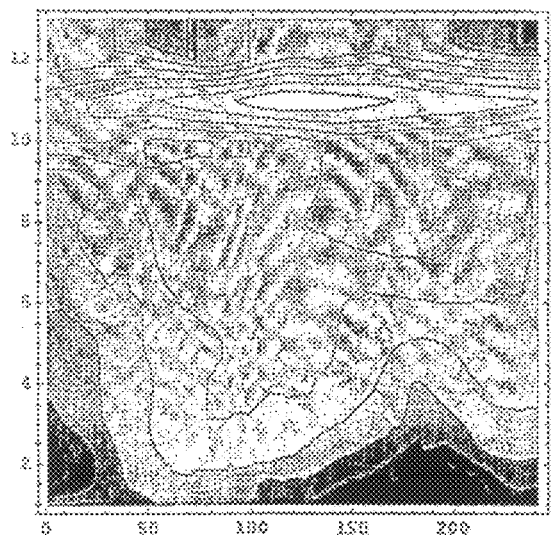
Figure 8C:
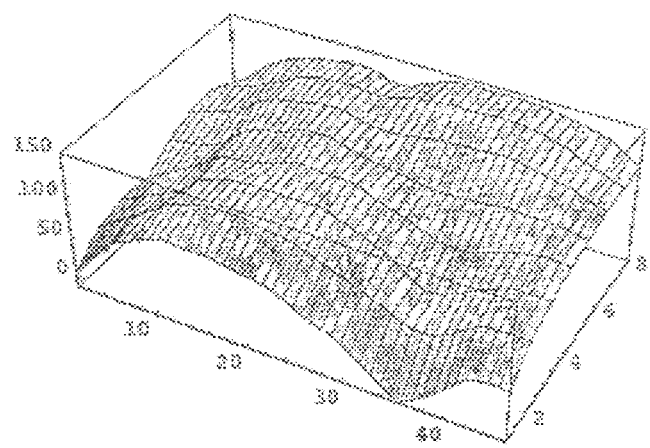
Figure 8D:
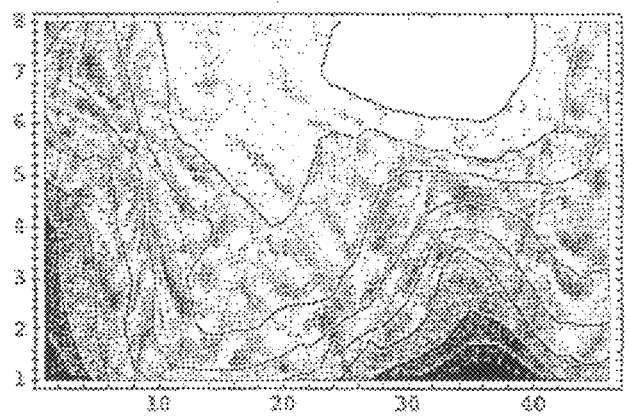
Figure 8E:
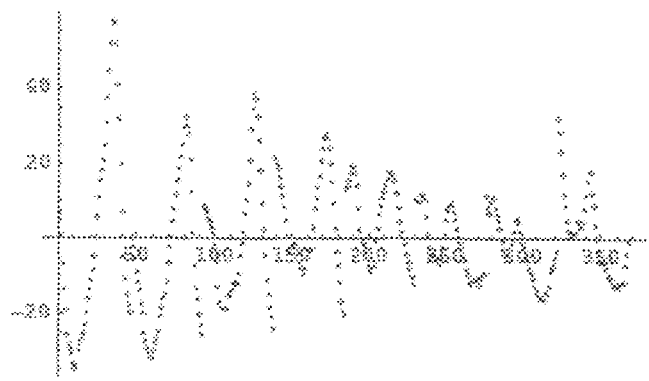

FIG. 6 shows an electron micrograph (25-times magnification) of pellets with the batch designation SFD E 0724, which do not fulfill the criteria according to the invention for a pellet core with a smooth surface.

FIG. 7 presents data obtained using a laser profilometer, characterizing the surface of a pellet with the batch designation SFD E 0724. FIG. 7 A is a graphical representation of the measurement results as a surface graph. FIG. 7 B shows the measurement results as a contour diagram. FIG. 7 C shows a surface graph based on a reduced data set. FIG. 7 D shows the corresponding contour diagram. FIG. 7 E shows the deviations of the measured points of the reduced data set from the ideal surface determined by the method of least squares.

FIG. 8 presents data obtained using a laser profilometer, characterizing the surface of another pellet with the batch designation SFD E 0724. FIG. 8 A is a graphical representation of the measurement results as a surface graph. FIG. 8 B shows the measurement results as a contour diagram. FIG. 8 C shows a surface graph based on a reduced data set. FIG. 8 D shows the corresponding contour diagram. FIG. 8 E shows the deviations of the measured points of the reduced data set from the ideal surface determined by the method of least squares.

Figure 9:
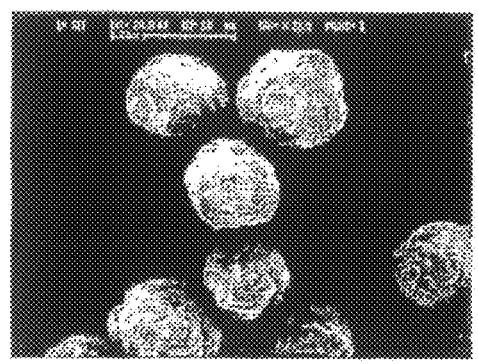
Figure 10A:
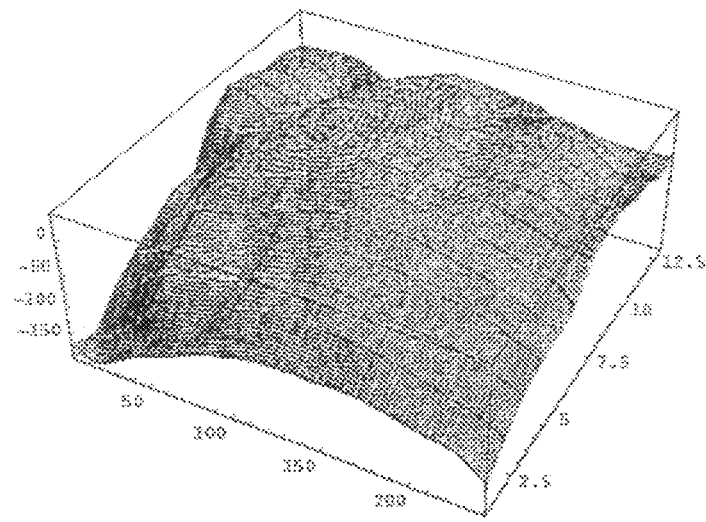
Figure 10B:
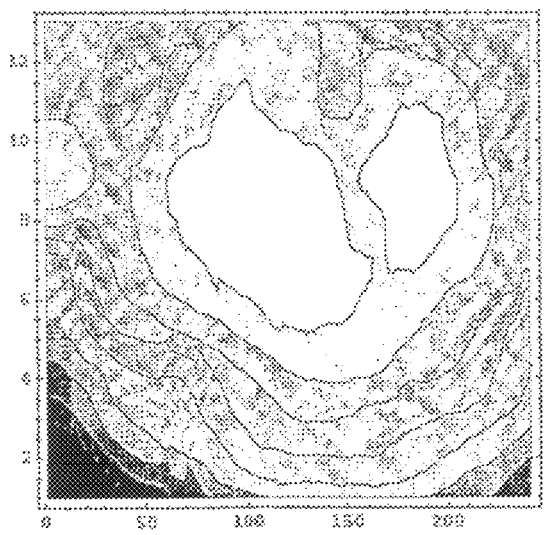
Figure 10C:
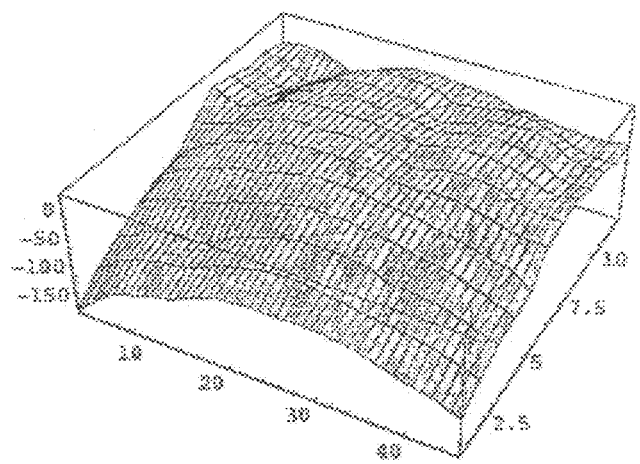
Figure 10D:
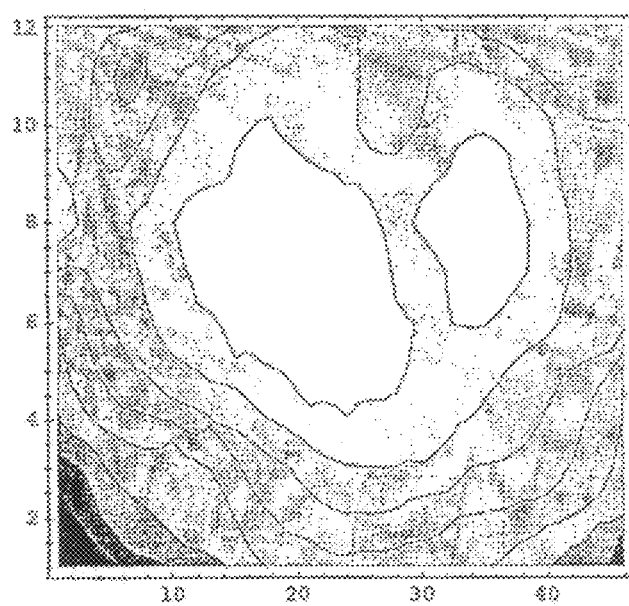
Figure 10E:
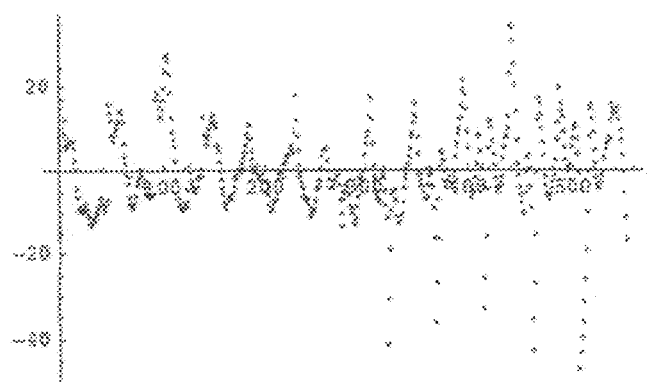

FIG. 9 shows an electron micrograph (25-times magnification) of pellets with the batch designation SFD E 0718, which do not fulfill the criteria according to the invention for a pellet core with a smooth surface.

FIG. 10 presents data obtained using a laser profilometer, characterizing the surface of a pellet with the batch designation SFD E 0718. FIG. 10 A is a graphical representation of the measurement results as a surface graph. FIG. 10 B shows the measurement results as a contour diagram. FIG. 10 C shows a surface graph based on a reduced data set. FIG. 10 D shows the corresponding contour diagram. FIG. 10 E shows the deviations of the measured points of the reduced data set from the ideal surface determined by the method of least squares.

FIG. 11 presents data obtained using a laser profilometer, characterizing the surface of another pellet with the batch designation SFD E 0718. FIG. 11A is a graphical representation of the measurement results as a surface graph. FIG. 11B shows the measurement results as a contour diagram. FIG. 11C shows a surface graph based on a reduced data set. FIG. 11D shows the corresponding contour diagram. FIG. 11E shows the deviations of the measured points of the reduced data set from the ideal surface determined by the method of least squares.

Figure 12:
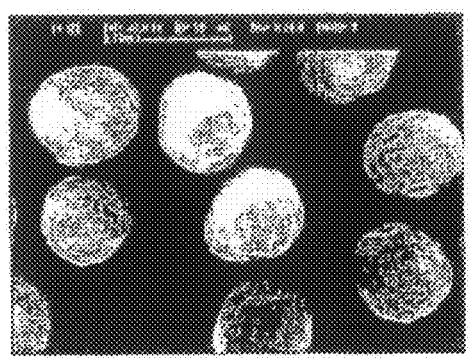
Figure 13A:
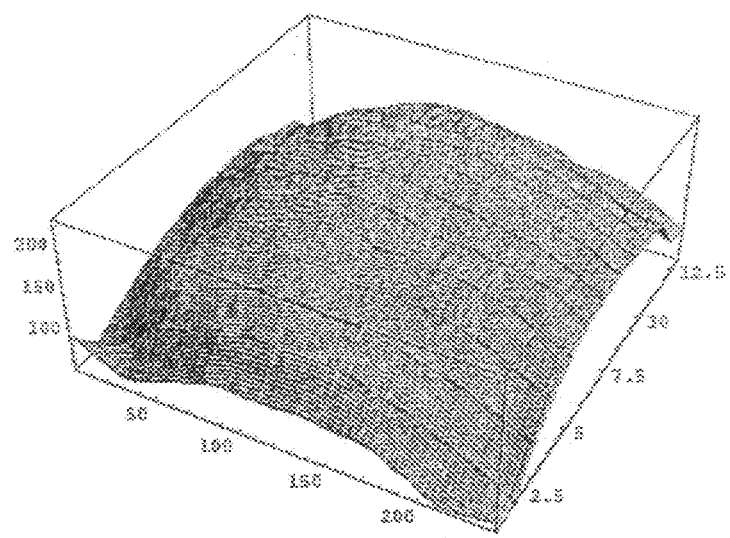
Figure 13B:
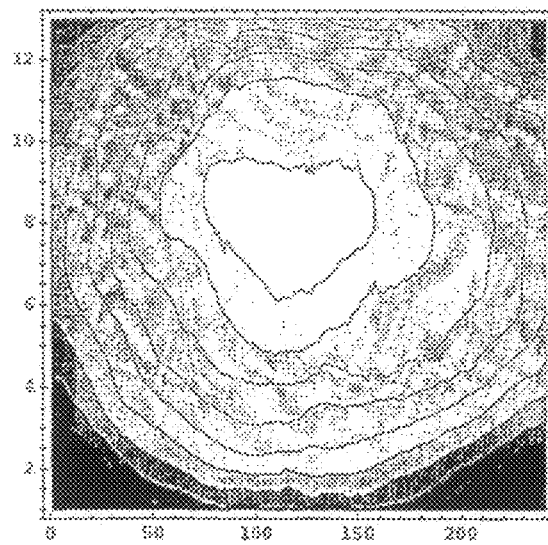
Figure 13C:
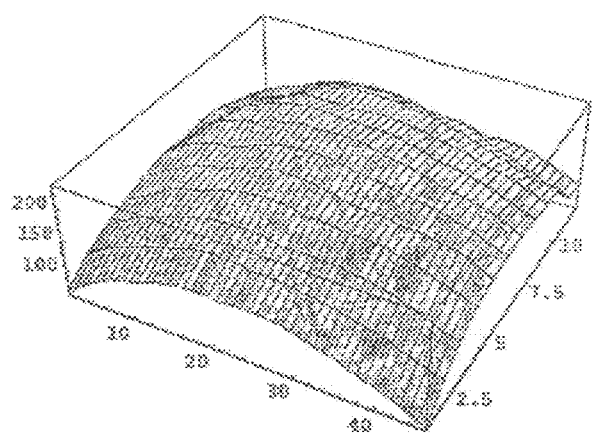
Figure 13D:
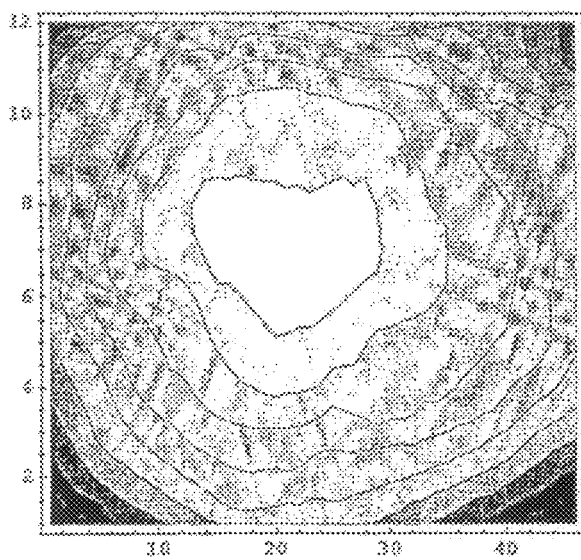
Figure 13E:
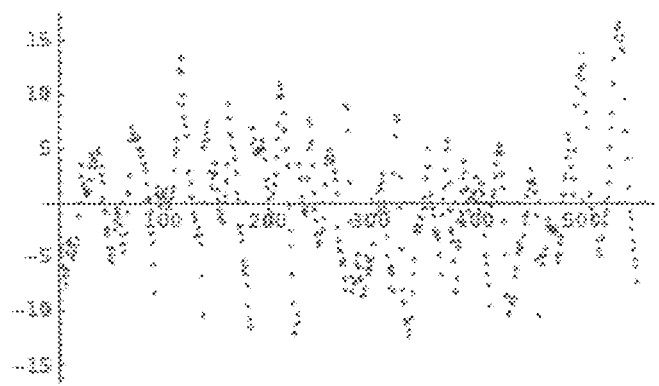

FIG. 12 shows an electron micrograph (25-times magnification) of pellets with the batch designation SFD E 0572, which do not fulfill the criteria according to the invention for a pellet core with a smooth surface.

FIG. 13 presents data obtained using a laser profilometer, characterizing the surface of a pellet with the batch designation SFD E 0572. FIG. 13 A is a graphical representation of the measurement results as a surface graph. FIG. 13 B shows the measurement results as a contour diagram. FIG. 13 C shows a surface graph based on a reduced data set. FIG. 13 D shows the corresponding contour diagram. FIG. 13 E shows the deviations of the measured points of the reduced data set from the ideal surface determined by the method of least squares.

Figure 14:
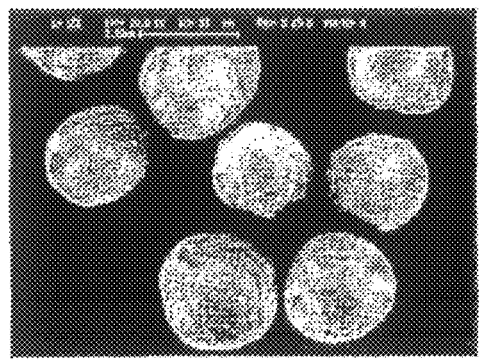
Figure 15A:
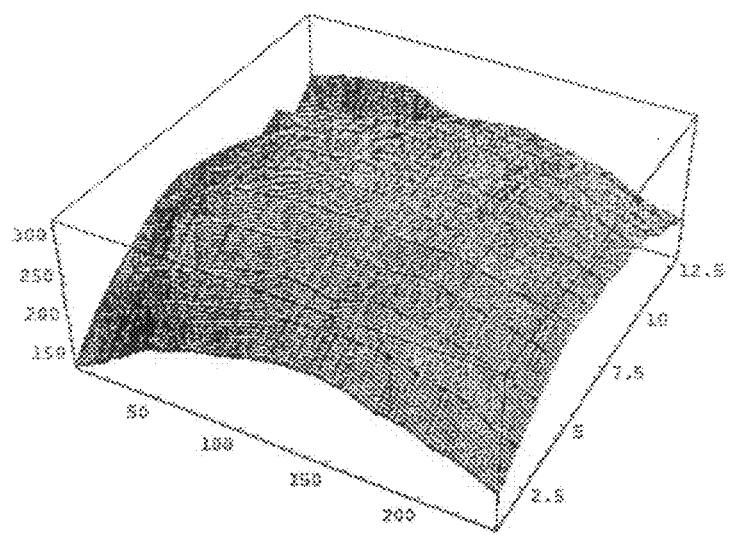
Figure 15B:
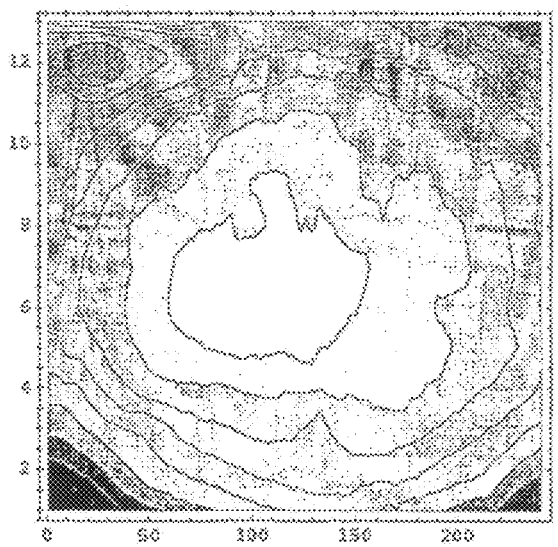
Figure 15C:
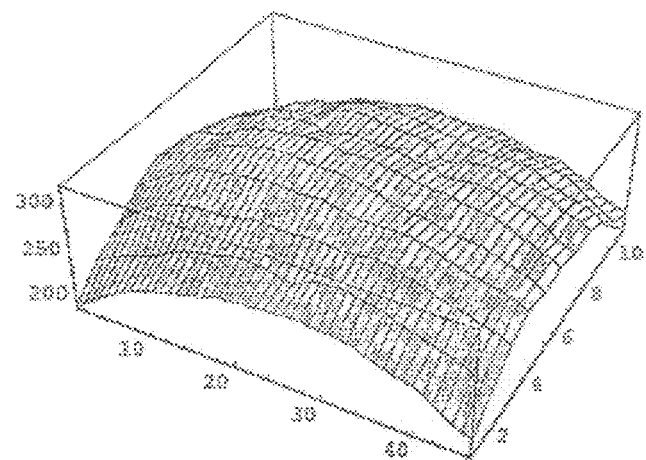
Figure 15D:
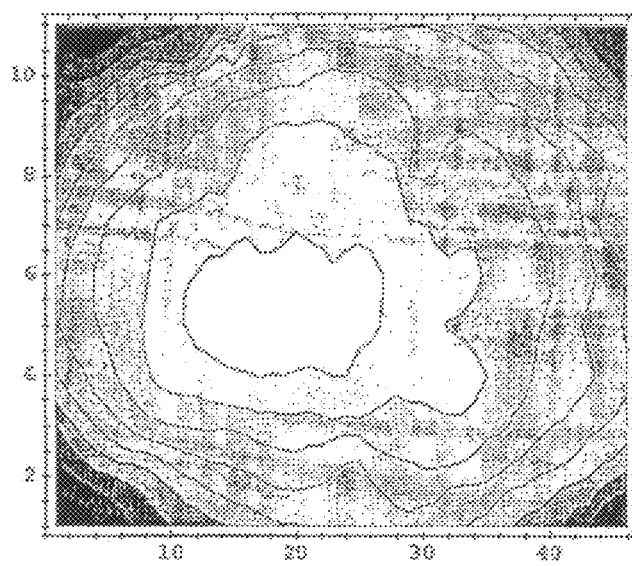
Figure 15E:
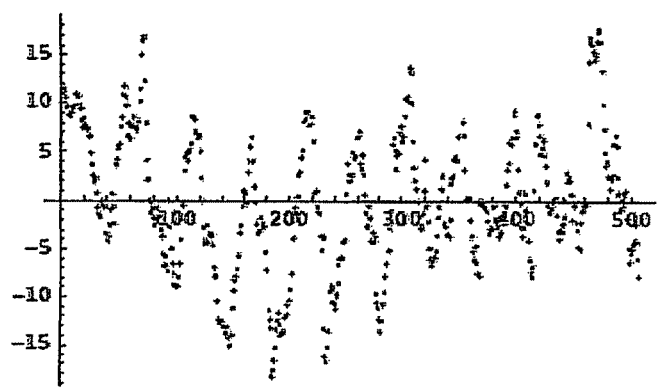
Figure 16A:
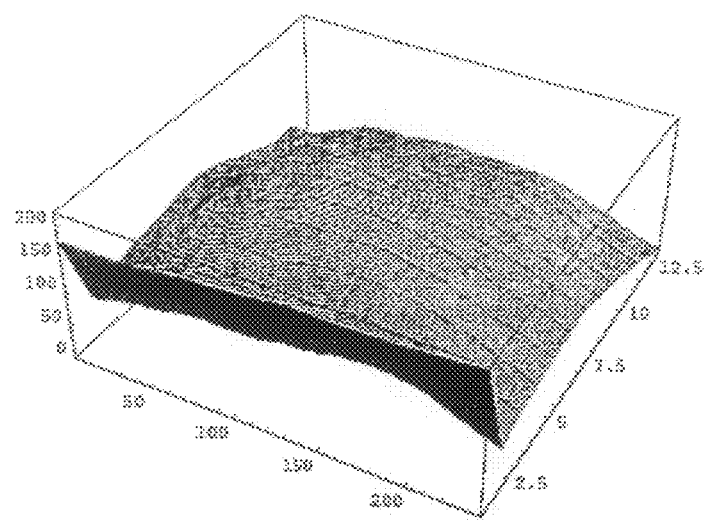
Figure 16B:
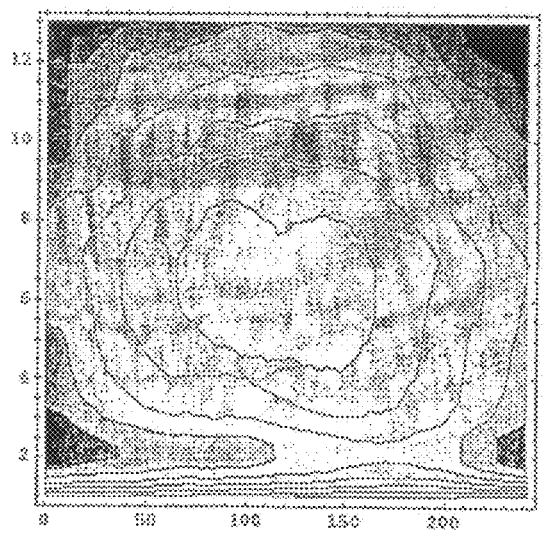
Figure 16C:
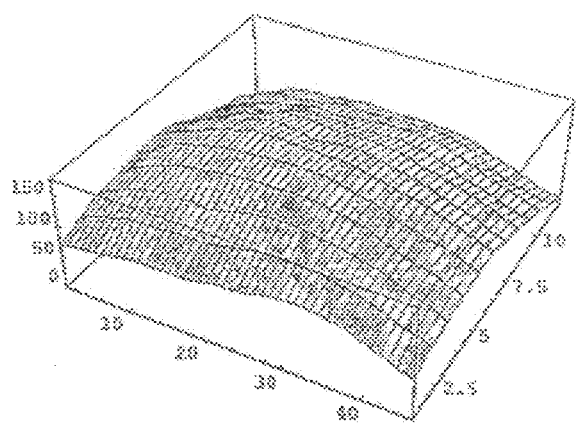
Figure 16D:
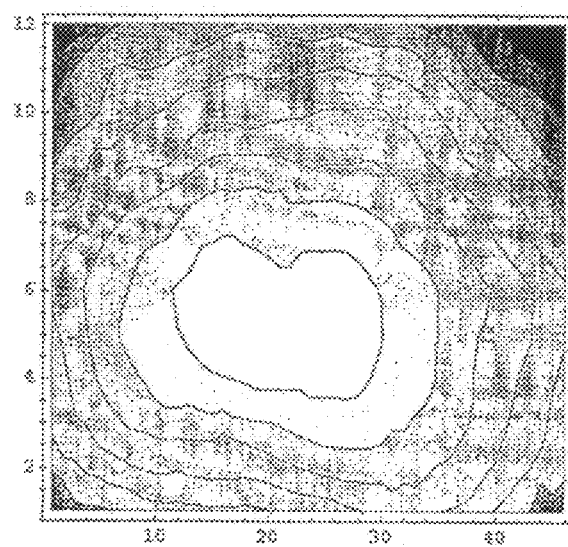
Figure 16E:
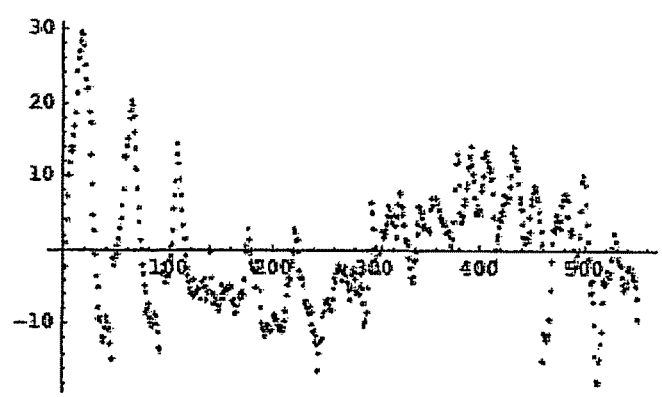

FIG. 14 shows an electron micrograph (25-times magnification) of pellets with the batch designation SFD E 0614, which do not fulfill the criteria according to the invention for a pellet core with a smooth surface.

FIG. 15 presents data obtained using a laser profilometer, characterizing the surface of a pellet with the batch designation SFD E 0614. FIG. 15 A is a graphical representation of the measurement results as a surface graph. FIG. 15 B shows the measurement results as a contour diagram. FIG. 15 C shows a surface graph based on a reduced data set. FIG. 15 D shows the corresponding contour diagram. FIG. 15 E shows the deviations of the measured points of the reduced data set from the ideal surface determined by the method of least squares.

FIG. 16 presents data obtained using a laser profilometer, characterizing the surface of another pellet with the batch designation SFD E 0614. FIG. 16 A is a graphical representation of the measurement results as a surface graph. FIG. 16 B shows the measurement results as a contour diagram. FIG. 16 C shows a surface graph based on a reduced data set. FIG. 16 D shows the corresponding contour diagram. FIG. 16 E shows the deviations of the measured points of the reduced data set from the ideal surface determined by the method of least squares.

DETAILED DESCRIPTION OF THE INVENTION

Definitions

Some technical terms used in the description and the claims are explained below.

The expression "core" of a pharmaceutical pellet is to be understood here as meaning that the entire inner portion of the pellet is enclosed beneath a coating that controls the pH-independent release of the active substance. The core can be homogeneous or can have an internal structure. Examples include cores where the active substance is distributed homogeneously in a carrier material; cores where the active substance is distributed together with one or more excipients in a carrier material; seed cores coated with a layer of active substance, where the layer of active substance can contain one or more excipients along with the active substance; and cores of the type stated above, which additionally have one or more coatings under the release-controlling coating, for example protective coatings or separating layers of water-soluble excipients, such as water-soluble film-forming agents.

Any biologically active substances, such as substances with therapeutic and/or prophylactic effects, which can be administered orally, can be considered as active substances according to the invention.

The core of a pharmaceutical pellet typically has a diameter in the range from 0.2 to 2 mm, in particular from 0.4 to 1.6 mm and quite especially from 0.4 to 1.4 mm.

A pellet or a core is described as spherical if the length-width ratio (i.e. the ratio of the length (largest dimension) of the pellet or core, divided by the width (smallest dimension), determined at an angle of 90° to the length) is less than about 1.4.

Preferably the length-width ratio of a spherical particle is less than about 1.3, more preferably less than about 1.2, even more preferably less than about 1.1 and in particular less than about 1.05.

According to the invention, the spherical core of the pharmaceutical pellet, which contains the active substance, and typically also the pellet itself have a smooth surface. This means that the surface roughness does not exceed a defined limit. The roughness also describes the deviation of a real surface from an ideal smooth surface.

According to the invention, it proved desirable to scan a suitable segment of the surface of the pellet core or of the pellet, and in particular by optical methods. The results of such scanning can then yield a numerical value for the roughness. More precisely, the surface profile is investigated for a segment of the surface of the pellet core or of the pellet. As far as possible the segment should be selected so that it is representative of the surface of the particle. Thus, measurements are performed on a segment of the surface corresponding to 5 to 50%, in particular 5 to 25%, and especially 5 to 15% of the total surface of the pellet. For this surface segment, measurement points are established that correspond to a grid. Points of the grid are typically between 2.5 and 50 µm, in particular between 12.5 and 50 µm apart. The number of measurement points is typically in the range from 50 to 5000.

The data obtained are then compared with an ideal surface. For this it is assumed that the surface region being measured can be represented by a segment of a spherical surface. This idealized spherical surface can be determined mathematically by calculating the segment from a spherical surface that is the best fit with the experimentally determined topography. The function that is minimized is the root-mean-square distance of the measured points of the profile from the spherical surface. The free parameters are then the coordinates of the center of the sphere ($x_{0s}$, $y_{0s}$, $z_{0s}$) and the radius of the sphere R. The roughness can then finally be determined from the distances $d_i$ of the measured points of the profile in the ideal spherical surface. For this, a root-mean-square value $$\sigma_d = \sqrt{\Sigma_{i=1}^N d_i^2}/\sqrt{N}$$

is determined. In the present application $\sigma_d$ is termed the "mean roughness". For a smooth pellet core or a smooth pellet the mean roughness is typically less than 10 µm and preferably less than 7.5 µm. The relative mean roughness, i.e. the roughness divided by the radius of the sphere R, is preferably less than 2%, in particular less than 1.5% and quite especially preferably less than 1.2%.

Based on the measurements described above, the smoothness of the surface of a core containing an active substance can also be described with additional parameters. One parameter is the maximum deviation, i.e. the maximum absolute distance of a point of the profile from the ideal smooth surface. This value is preferably not more than 40 µm, in particular not more than 30 µm, even more preferably not more than 25 µm and quite especially preferably not more than 20 µm.

For a spherical pellet, it is also possible to state a maximum relative deviation. This means the maximum absolute deviation, divided by the radius of the sphere determined within the scope of optimization. Preferably the maximum relative deviation is not more than 5%, in particular not more than 3%.

A preferred method of determination of the roughness of a pellet will be described later.

pH-independent release of the active substance means that the release of the active substance does not vary significantly when pellets according to the invention are exposed to media with pH values such as are encountered in various segments of the gastrointestinal tract. These pH values range from 1.0 to 8.0.

Methods for determining the release of the active substance are described in the USP (United States Pharmacopeia) and in the Ph.Eur. Reference will be made to these methods here. In particular, a paddle-apparatus is used. The stirring speed is 50 revolutions per minute. The temperature of the test medium is 37° C. A phosphate buffer with a pH value of 6.8 is used as the test medium.

According to one aspect of the invention, release of the active substance takes place with a defined profile. The profile has a lag-phase, and during the lag-phase a proportion of 5 wt. % or less of the active substance is released. The lag-phase lasts 60 to 840 minutes, preferably 60 minutes to 540 minutes.

According to one aspect of the invention, after a lag-phase, at least 80 wt. % of the active substance still remaining is released within 60 minutes, preferably within 30 minutes. According to another aspect of the invention, the release of the active substance, after a lag-phase, is between 3 and 25 wt. % per hour, preferably between 3 and 15 wt. % per hour and in particular between 3 and 6.5 wt. % per hour.

Preferred Embodiments

Pellets

Pharmaceutical pellets according to the invention have a core, which contains one or more active substances. Active substances with high water solubility are preferred. Water-soluble salts of sparingly water-soluble active substances are further preferred. An example of this is ADD 006, with a water-solubility of approx. 210 mg/ml at 25° C.

The core also typically contains one or more binders. Water-soluble binders are preferred. These include calcium carboxymethyl cellulose, polymers based on acrylic acid (Carbopol), gelatin, hydroxyethyl cellulose, hydroxypropyl cellulose, hydroxypropyl methylcellulose, polyethylene glycol (macrogol), methyl cellulose, sodium carboxymethyl cellulose, sodium carboxy-methyl starch, polyoxypropylene-polyoxyethylene block polymers (poloxamers), polyvinyl alcohol, polyvinyl pyrrolidone (povidone) and starch. Preferred binders include gelatin, sodium carboxymethyl cellulose and polyvinyl pyrrolidone (povidone). Polyvinyl pyrrolidone is quite especially preferred. Polyvinyl pyrrolidone (povidone) is commercially available in a suitable form, for example as Collidon 30.

The core can additionally contain carriers or fillers. Carbohydrates are suitable, for example. As examples, we may mention water-soluble carbohydrates, such as dextran, dextrin, dextrose (glucose), fructose, lactose, maltodextrin, mannitol, sucrose, sorbitol and xylitol. Another example of a carrier or filler is microcrystalline cellulose.

The core can contain other optional ingredients. It can additionally contain both water-soluble and water-insoluble excipients. These include preservatives, physical stabilizers and chemical stabilizers, such as acid, basic or buffering components. It can also contain wetting agents and solubilizers. The cores can additionally contain osmotically active substances. This is preferred in particular in the case of active substances that are only slightly water-soluble. In this case an osmotically active substance can serve as an entraining agent. The optional constituents also include antisticking agents.

The pellet core can be coated with a protective layer. Preferred materials are water-soluble polymers, in particular hydroxypropyl methylcellulose.

According to the invention, the pellet cores, which are provided with the coating controlling the release of the active substance, should be as round as possible and as smooth as possible. So as to be able to verify the quality of pellet cores or pellets, an upper limit is therefore stipulated for the roughness. In order to determine the roughness of a pellet, the surface profile of a suitably selected segment is recorded, preferably using contactless optical methods, for example using an autofocusing laser profilometer, such as a UBM laser profilometer. Its mode of operation can be described as follows:

A laser beam is projected by a lens system onto the surface of the structure to be measured (the surface segment of a pellet core or pellet). The sensor head consists of a lens system and two photodetectors arranged symmetrically to its optical axis. At the level of the focal point of the lens system, a diaphragm is mounted, which trims the image of the laser beam on one side. If the sample is at the focus of the sensor, the laser beam reflected on the sample will be focused in the region of the diaphragm and will not be trimmed. In this case both detectors measure the same intensity. If the sample is outside of the focal range, no sharp image of the laser beam is produced. Instead, there is a wider intensity distribution in the region of the diaphragm, which is trimmed by the latter. Consequently, the detectors measure different intensities. To measure the height difference $\Delta h$ the sensor head is moved vertically until the sample is again in focus and both detectors measure the same intensity. The vertical displacement of the sensor, effected by means of magnetic positioning elements, then represents the height difference. While the sensor head measures the height of the sample continuously, the latter is moved along by a motorized x-y table under the sensor head. The lateral resolution of the profilometer is 0.5 µm, and is essentially determined by the beam diameter. The vertical accuracy is stated by the manufacturer to be 100 nm.

The surface segment to be measured is specified so as to cover typical profile structures. For example, for a spherical pellet with a radius between 400 and 600 µm, a surface region of 600 µm×600 µm can be scanned. Scanning takes place in thirteen parallel line scans at intervals of 50 µm. For the individual line scans, scanning is at intervals of 2.5 µm, which leads to a total number of 241 points per line scan.

Mathematical evaluation of the data is typically associated with data reduction. During the commencement of line scanning, the optical instrument must first achieve focusing on the surface. For this reason the first measurements suffer from uncertainties. Therefore the first fifteen measurement points of each line scan are excluded from the analysis. Because sometimes in the first line scans no convergence of the focusing procedure is achieved, possibly due to the fact that the starting point or end point of the line scan lies outside of the perimeter of the spherical particle, such line scans are excluded from the analysis. Similar focusing problems sometimes occur in the last line scans, which are then also excluded from the analysis.

The data from line scanning are thinned by a factor of 5, which leads to a reduction of the 241-15 measurement points per line to typically 45 measurement points per line. It has been found experimentally that this does not lead to any significant loss of a surface profile structure, since typical profile structures extend over 50 to 100 µm.

As already stated, a segment from an ideal spherical surface is then fitted, by the method of least squares, to the reduced set of data points. Deviations from the ideal surface are taken as a measure of the roughness. For this, a mean roughness $\sigma_d$ can be defined.

This textural parameter corresponds to the usual definition of the root-mean-square roughness $R_{RMS}$, which is widely adopted for planar texturized surfaces. In addition, a relative root-mean-square roughness is also defined, which can be calculated from the mean roughness $\sigma_d$ defined above and the radius of the sphere R according to $\sigma_d/R$. The relative root-mean-square roughness is also stated as a percentage in the present application ($\sigma_d/R \times 100\%$).

Pellet cores with a smooth surface, as described previously, are according to the invention provided with a coating, which controls the release of the active substance independently of the pH.

The coatings for pH-independent release of the active substance preferably contain a polymer, which is selected from ammonium-methacrylate copolymer, cellulose acetate-butyrate, cellulose acetate, cellulose acetate-propionate, ethyl cellulose, poly(ethylacrylate-methylacrylate) and polyvinyl acetate. Polyvinyl acetate is especially preferred. When using these film-forming agents, the release of the active substance from the pellets can be modified by the layer thickness of the applied film and by selection of suitable additional excipients (in particular pore-forming agents).

Accordingly, the coating for controlling the pH-independent release of the active substance can contain pore-forming agents, in particular water-soluble polymers or other water-soluble compounds.

The coating for controlling the pH-independent release of the active substance can also contain plasticizers. These include acetyltributyl citrate, triacetin, acetylated monoglyceride, rapeseed oil, olive oil, sesame oil, acetyltriethyl citrate, glycerol-sorbitol, diethyl oxalate, diethyl malate, diethyl fumarate, dibutyl succinate, diethyl malonate, dioctyl stalate, dibutyl sebacate, diethyl citrate, tributyl citrate, glycerol, tributyrate, polyethylene glycol, propylene glycol and mixtures thereof.

The coating can also contain a separating agent. An example is talc.

The pellets according to the invention can also have an outer protective coating. Preferred materials for this are water-soluble polymers, in particular hydroxypropyl methylcellulose.

Multiparticulate dosage forms can be provided using the pellets according to the invention. For example, capsules can be filled with the pellets. However, tablets can also be produced from the pellets.

Preferred Embodiments

Methods of Production

Methods of production are also provided according to the invention. These include methods for the production of pellet cores and methods for the coating of pellet cores, but the invention is not restricted to a particular manner of production.

One method for the production of pellet cores is fluidized-bed agglomeration. Granulation can be carried out without seed cores. In this way, pellet cores can be produced with a comparatively very high proportion of active substance. For example, pellet cores can be produced that contain 80 parts by weight or more, preferably 90 parts by weight or more, of active substance and in addition contain a binder. Using a sifting device, by means of which pellet cores are removed from the process continuously, it is possible to achieve a very narrow granulometric distribution. For example, a pellet core product can be obtained in which 95 wt. % or more, preferably 99 wt. % or more, of the pellet cores have a size between 100 and 300 µm or even between 200 and 300 µm.

For carrying out the method, a liquid, preferably aqueous solution or dispersion with an active substance and optionally one or more excipients, such as a binder, is injected from below into an empty fluidized-bed unit at the start of the process. Seed cores for pelletization are formed by spray-granulation. Through deposition of further material, the cores finally reach a size such that they are discharged from the unit via a sifting device.

Suitable equipment for carrying out fluidized-bed agglomeration is described in EP 163 836 B1, EP 332 031 B1 and EP 332 929 B1.

Another method for the production of pellet cores comprises the preparation of seed cores and the subsequent application of a layer of active substance (layering). An active substance, optionally together with other ingredients, is applied to cores. This can take place in a fluidized-bed unit, with feed of a powdered material and a liquid, which binds the pulverulent ingredients to the cores. The powder can be an active substance or a mixture of an active substance and one or more excipients. The liquid can be water or an organic solvent; the liquid can also be a solution or dispersion.

In addition, a method for the production of pellet cores containing an active substance is preferred in which seed cores are coated, for example in fluidized-bed apparatus, with a solution or dispersion containing an active substance and optionally one or more excipients.

The production of pellet cores described above, by applying a layer of active substance on seed cores, preferably takes place in fluidized-bed apparatus with a Wurster insert (according to the Wurster process).

Another method for the production of pellet cores comprises the preparation of a powdered starting material in a first stage. The powdered starting material includes a carrier. The powdered starting material preferably undergoes treatment, for example in a shearing mixer, to break up aggregates. The powdered starting material can also be a mixture of a carrier and one or more other ingredients of the pellet cores that are being produced, for example binders. In this case the preparation of the powdered starting material typically involves mixing of the components.

It is preferable to use a powdered starting material with a limited grain size. In particular, the powdered starting material includes a carrier that has a limited grain size. Furthermore, a narrow granulometric distribution is preferred for the powdered starting material and in particular for the carrier.

For example, in the production of pellet cores with a size from 300 to 500 µm it has proved advantageous to use a powdered starting material, in particular a carrier, for which the oversize at a mesh size of 160 µm is less than 10 wt. % and in particular less than 5 wt. %. Powdered starting material, in particular a powdered carrier, are further preferred for which the oversize at a mesh size of 40 µm is in the range from 50 to 80 wt. %. Especially preferably, the oversize at a mesh size of 160 µm is in the range from 1 to 5 wt. % and at a mesh size of 40 µm is in the range from 50 to 70 wt. %.

The powdered starting material can be moistened before the pelletization stage. For this, a pharmaceutically acceptable diluent is added to it. It can be the same diluent as that used in the subsequent pelletization stage, or it can be a diluent of a different composition. The diluent can be an organic liquid. Preferably it is water or an aqueous solution or dispersion. The liquid can contain, as ingredients, a binder and/or an active substance and/or other core ingredients. The amount of the pharmaceutically acceptable diluent is preferably such that a wetted powdered starting material is achieved, with the amount of liquid added being less than the amount that is required for the formation of granulated structures. It is preferable to ensure uniform moistening of the powdered starting material. This can be carried out using a suitable mixer, such as a shearing mixer.

If several powdered components are used, mixing and premoistening can take place in one step, for example in a high-speed mixer.

In the pelletization stage, pellets are formed from the optionally premoistened starting material, with addition of a pharmaceutically acceptable liquid diluent. The diluent must meet the same quality criteria as for the diluent used for premoistening.

The diluent can contain an active substance.

It is also possible to add powdered ingredients, for example powdered active substance, during pelletization, if the process ensures homogeneous, thorough mixing. As the pellets according to the invention contain an active substance, this must either be present in the powdered starting material or it must be added during pelletization as a constituent of the diluent or in powdered form. Combinations of these measures are also possible.

According to a preferred embodiment, the method comprises the following stages:

(a) preparation of a powdered starting material, which includes a carrier;
(b) feed of the powdered starting material, which is optionally wetted with a pharmaceutically suitable liquid diluent, into a device that has:
a rotary chamber with a cylindrical wall extending axially,
a device for leading air through the rotary chamber from the bottom,
a spraying device for feeding liquid into the chamber,
one or more inlets for introducing the powdered mixture,
a rotor, which rotates about a vertical axis, the rotor being arranged in the rotary chamber, and has a central horizontal surface and, in at least the outer third of the rotor, the form of a conical surface with a slope, directed outward and upward, between 10° and 80°, with the conical surface having a circular upper edge, which is in a plane that is perpendicular to the axis of rotation,
a multiplicity of guide vanes each with an outer end that is fixed statically to the cylindrical wall of the rotary chamber above the plane that is formed by the upper edge of the conical surface of the rotor, and an inner end, which extends into the rotary chamber and is arranged tangentially to the cylindrical wall of the rotary chamber and has, in cross-section to the axis of rotation, essentially the form of a circular arc or a spiral,
(c) rotation of the rotor, so that the product, which is circulated for a sufficient length of time through kinetic energy, moves from the rotor to the inner surface of the guide vanes, before it drops back onto the rotor, while optionally air is supplied and/or a pharmaceutically acceptable liquid is sprayed into the rotary chamber, so that solid pellets with a desired diameter are formed.

A suitable device for carrying out the first method for the production of pellet cores is described in DE 197 50 042 A1.

During pellet formation, a pharmaceutically acceptable diluent is supplied, as already described. The amount is selected depending in particular on the components of the starting material, the desired pellet size and other operational variables, for example the amount of air supplied.

The pellet cores finally obtained are dried.

It is preferable to verify whether the pellet cores produced satisfy the requirements of the invention. In particular it is verified whether a pellet core product according to the invention is produced. This means that preferably the pellets of the pellet core product obtained, which consists of a collection or a multiplicity of pellet cores, are primarily spherical and have smooth surfaces. Preferably at least 90% of the pellet cores of a pellet core product fulfill the requirements according to the invention regarding spherical shape and smooth surface.

The pellets obtained can find application as a pellet product that comprises a multiplicity of pellets. A pellet product comprises a collection of pellets, typically 50 or more, preferably 100 or more pellets. A pellet product according to the invention comprises primarily pellets that fulfill the criteria according to the invention. Preferably at least 90%, in particular at least 95% and quite especially preferably at least 98% of the pellets have a length-width ratio of less than about 1.4, preferably less than about 1.3, more preferably less than about 1.2, even more preferably less than about 1.1 and in particular less than about 1.05. Pellets that have the preferred length-width proportions, preferably also meet the other requirements for pellets according to the invention, and especially the requirements that are specified in the claims and in the description.

The pellet cores obtained according to one of the above methods can optionally be provided with one or more coatings by known methods. These include coatings obtained from water-soluble film-forming agents.

The pellet cores—with or without coating, such as a coating obtained from a water-soluble film-forming agent, are coated with a polymer for pH-independent release of the active substance.

According to the invention, tablets can also be produced, by compressing pharmaceutical pellets, optionally together with excipients. It is then possible, according to the invention, to obtain tablets for which the release curve of the active substance has undergone parallel displacement in comparison with the release curve from the pellets. In other words the lag-phase that arises during release from the tablets is shorter than the lag-phase arising during release from the pellets, whereas the gradient of the release curve remains essentially unchanged. The release behavior can be measured, as has already been described.

The invention is explained by the following production examples, examples and test examples. ADD 006 is used as the active substance; its water solubility at 25° C. is approx. 210 mg/ml.

Production Example 1

The example relates to the production of pellets containing ADD 006.

The following starting materials are used for the production of pellet cores with the active substance ADD 006:

| | |
|---|---|
| Sugar spheres (seed cores) | 300 g |
| Syloid 244 FP (precipitated silica) | 45 g |
| ADD 006 | 1200 g |
| Demineralized water | 2757 g |

A proportion of the demineralized water (2457 g) is heated to approx. 60° C. The ADD 006 is dissolved in the heated water. The silica (Syloid 244 FP) is suspended in another portion of the demineralized water (300 g) using a homogenizer for ten minutes. Then the silica dispersion is poured into the solution of active substance. The resultant mixture (coating dispersion) is stirred at a temperature of approx. 50° C.

For coating, the seed cores are put in a fluidized-bed coating device (Glatt GPCG 1). Then the coating dispersion is sprayed on at an initial spraying rate of 6 g/min. The spraying rate is then increased to 8-10 g/min. The inlet air temperature during coating is approx. 55° C.

After the coating dispersion has been sprayed on, the cores obtained are dried in the apparatus for ten minutes at an inlet air temperature of approx. 60° C. Then the cores are taken out and dried further at 45° C. overnight.

In the manner described above, ADD 006 cores can be obtained with a content of active substance of 77.67 wt. %.

The cores obtained, containing the active substance, can be provided with a coating that controls the pH-independent release of the active substance. Polyvinyl acetate is a suitable coating material. Example preparation starts from the following starting materials:

| | |
|---|---|
| ADD 006 cores (as described above) | 300.00 g |

| | |
|---|---|
| Kollicoat SR 30 D (polyvinyl acetate dispersion) | 277.78 g (solids content: 83.33 g) |
| Avicel PH 105 (microcrystalline cellulose) | 5.00 g |
| Triethyl citrate | 8.33 g |
| Talc | 8.33 g |
| Demineralized water | 280.00 g |

To prepare the coating dispersion, first the microcrystalline cellulose is dispersed in the demineralized water using a homogenizer and stirred for five minutes. Then triethyl citrate and talc are added to the dispersion and the dispersion is homogenized again for ten minutes. The polyvinyl acetate dispersion is sieved and the dispersion of excipients obtained previously is added to it, stirring slowly. The coating dispersion obtained is stirred for one hour, before the film coating of the cores is begun.

The coating is applied in a fluidized-bed coating device (Glatt GPCG 1). The cores containing the active substance are heated to approx. 30° C. Then the coating dispersion is sprayed on at a spraying rate of approx. 7-8 g/min. The inlet air temperature is approx. 35° C.

In the same conditions as previously, next a first outer pellet phase is applied, using the following excipients in the following amounts:

| | |
|---|---|
| Syloid 244 FP (precipitated silica) | 7.03 g |
| Pharmacoat 603 (hydroxypropyl methylcellulose) | 1.07 g |
| Demineralized water | 50.81 g |

Hydroxypropyl methylcellulose is dissolved in the water, and then the silica is added in portions, with stirring. After applying this dispersion on the coated pellets, the pellets are taken out of the fluidized-bed apparatus. The following ingredients are then added to them as second outer pellet phase:

| | |
|---|---|
| Syloid 244 FP (precipitated silica) | 4.13 g |
| Talc | 4.13 g |

The pellets to which these excipients have been added are mixed for five minutes in a diffusion mixer (Turbula T2C). The product obtained is finish-dried overnight in a ventilated stove at 60° C.

Production Example 2

The example relates to the production of pellets containing ADD 006 and the further processing of the pellets to tablets.

Pellet cores with the active substance ADD 006 are produced in the same way as in production example 1. For a preparation with a dose strength of 200 mg ADD 006, starting materials are used in the following proportions:

| | |
|---|---|
| Sugar spheres NF (seed cores) | 50.000 mg |
| ADD 006 | 200.000 mg |
| Colloidal silica | 7.500 mg |
| Subtotal | 257.500 mg |

The pellet cores containing the active substance are provided with a coating for controlled release. Two different formulations are investigated in this way. The proportions in the first formulation, based on cores containing 257.500 mg of active substance, are as follows:

| | |
|---|---|
| Polyvinyl acetate dispersion, solids | 75.100 mg |
| Talc (10%) | 7.500 mg |
| Triethyl citrate (10%) | 7.500 mg |
| Subtotal | 90.100 mg |

A smaller amount of plasticizer (triethyl citrate) is used in the second formulation for the controlled-release coating. The proportions of the formulation, based on pellet cores containing 257.500 mg of active substance, are as follows:

| | |
|---|---|
| Polyvinyl acetate dispersion, solids | 76.700 mg |
| Talc (10%) | 7.700 mg |
| Triethyl citrate (7.5%) | 5.800 mg |
| Subtotal | 90.100 mg |

On the basis of the formulations, coated pellets are produced, as described in production example 1. A protective coating (2%) is then applied on the pellets. The proportions of the components of this protective coating are as follows:

| | |
|---|---|
| Hydroxypropyl methylcellulose | 3.500 mg |
| Colloidal silica | 3.500 mg |
| Subtotal | 7.000 mg |

The pellets obtained are then used for making tablets. The tableting phase contains the following proportions of excipients:

| | |
|---|---|
| Microcrystalline cellulose | 105.9 mg |
| Lactose | 337.3 mg |
| Corn starch | 53.0 mg |
| Crospovidone | 26.5 mg |
| Colloidal silica | 1.6 mg |
| Magnesium stearate | 5.3 mg |
| Subtotal | 529.6 mg |

The pellets provided with the coating controlling the release of the active substance and the protective coating are mixed with the stated excipients and are compressed to form tablets. Tablets with a weight of 884.200 mg, which contain 200.000 mg ADD 006, are obtained.

Tablets of other dose strengths can be obtained correspondingly.

Example 1

The example relates to investigation of the release behavior of products according to the invention. In particular it is shown that the release profile can be adjusted by providing pellet cores according to the invention with coatings that control the release, and varying the composition of the coatings.

Release was determined in each case with a paddle apparatus (USP/Ph.Eur.) at a stirring speed of 50 revolutions per minute in phosphate buffer pH 6.8 as test medium at a temperature of 37° C.

Figure 1:
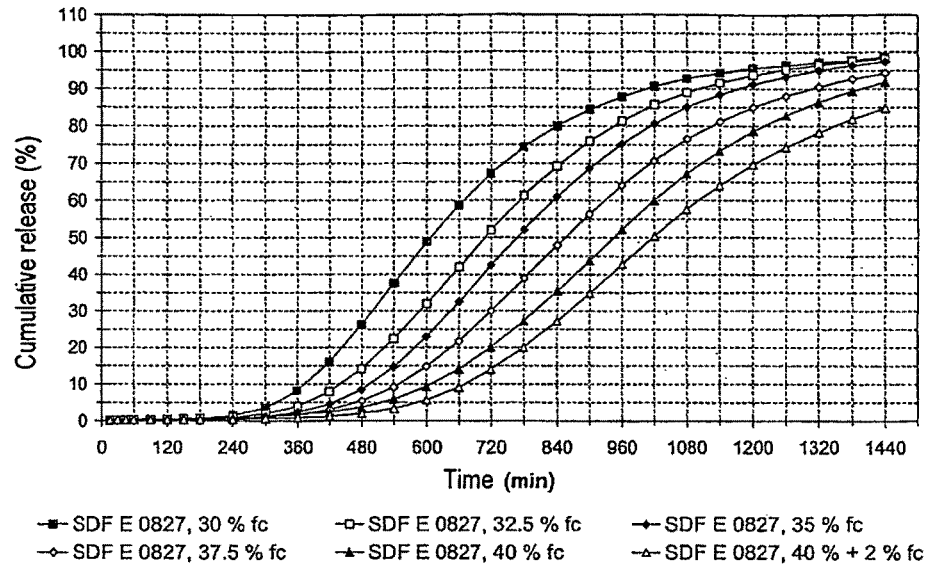
FIG. 1 shows the influence of the thickness of the release-controlling coating on the release of the active substance in the case of pellets containing the active substance ADD 006, with the coating consisting of polyvinyl acetate and, relative to the weight of the polyvinyl acetate, 10 wt. % triethyl citrate and 10 wt. % talc. The cumulative release (%) is plotted versus time (minutes). The percentage amount of coating material (polyvinyl acetate, triethyl citrate and talc in the composition stated above) relative to the weight of the pellet cores containing the active substance, for the individual batches, is given as a measure for the thickness of the coating.

First pellets were produced with the active substance ADD 006, as was described in production examples 1 and 2. These pellets were then coated to control release. A polyvinyl acetate dispersion containing talc (10 wt. %) and triethyl citrate (10 wt. %) was used for this. The thickness of the coating was varied by using different amounts of coating dispersion with polyvinyl acetate and 10 wt. % talc and 10 wt. % triethyl citrate, based in each case on the amount of solid polyvinyl acetate. Relative to the pellet cores containing the active substance, these amounts in the individual experiments were 30 wt. %, 32.5 wt. %, 35 wt. %, 37.5 wt. % and 40 wt. %. Pellets with a coating of 40 wt. % of the aforementioned polyvinyl acetate composition were in addition provided with 2 wt. % of a coating of hydroxypropyl methylcellulose and colloidal silica, the last-mentioned percentage by weight being calculated from the weight of the solid ingredients of the protective coating, relative to the weight of the pellets with the polyvinyl acetate coating. Samples of the individual preparations were then submitted to release tests. The results are shown in FIG. 1.

Example 2

The example relates to investigation of the release behavior of products according to the invention. In particular it is shown that the release profile can be adjusted by providing pellet cores according to the invention with coatings that control the release, and varying the composition of the coatings.

First, pellets were produced with the active substance ADD 006, as was described in production examples 1 and 2. These pellets were then coated to control release. A polyvinyl acetate dispersion containing talc (10 wt. %) and triethyl citrate (7.5 wt. %) was used for this. The thickness of the coating was varied by using different amounts of coating dispersion with polyvinyl acetate and 10 wt. % talc and 7.5 wt. % triethyl citrate, based in each case on the amount of solid polyvinyl acetate. Relative to the pellet cores containing the active substance, these amounts in the individual experiments were 30 wt. %, 32.5 wt. %, 35 wt. %, 37.5 wt. % and 40 wt. %. Pellets with a coating of 40 wt. % of the aforementioned polyvinyl acetate composition were in addition provided with 2 wt. % of a coating of hydroxypropyl methylcellulose and colloidal silica, the last-mentioned percentage by weight being calculated from the weight of the solid ingredients of the protective coating, relative to the weight of the pellets with the polyvinyl acetate coating.

Figure 2:
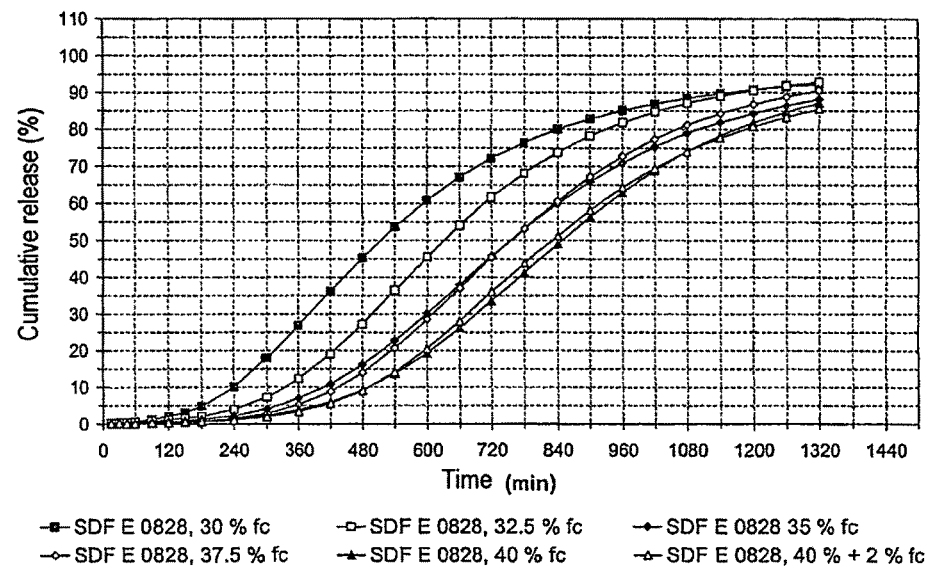
FIG. 2 shows the influence of the thickness of the release-controlling coating on the release of the active substance in the case of pellets containing the active substance ADD 006, with the coating consisting of polyvinyl acetate and, relative to the weight of the polyvinyl acetate, 7.5 wt. % triethyl citrate and 10 wt. % talc. The cumulative release (%) is plotted versus time (minutes). The percentage amount of coating material (polyvinyl acetate, triethyl citrate and talc in the composition stated above) relative to the weight of the pellet cores containing the active substance, for the individual batches, is given as a measure for the thickness of the coating.

Samples of the individual preparations were then submitted to release tests. The release tests were carried out as described in example 1. The results are shown in FIG. 2.

Example 3

The example relates to investigation of the release behavior of products according to the invention. In particular the example elucidates the effect of tableting on the release behavior.

Figure 3:
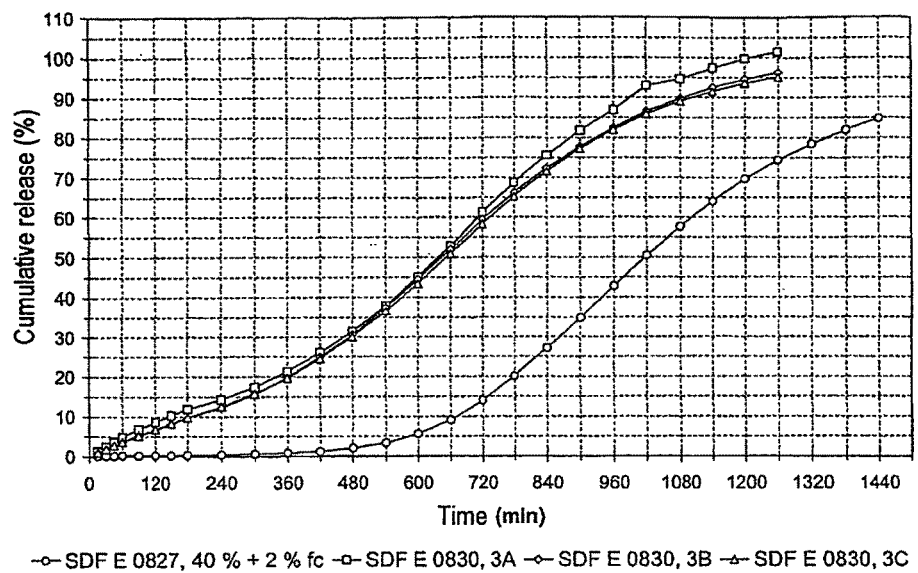
FIG. 3 shows the influence of the compression force on the release of the active substance from tablets with a diameter of 12 mm and a weight of 884.2 mg, which contain 200 mg ADD 006. The tablets were produced in each case using pellets that have a pellet core with the active substance ADD 006. The pellet core was coated with 40 wt. % of a coating consisting, relative to the weight of the pellet cores, of polyvinyl acetate, triethyl citrate (10 wt. %, relative to the weight of the polyvinyl acetate) and talc (10 wt. %, relative to the weight of the polyvinyl acetate) and a protective coating of hydroxypropyl methylcellulose and colloidal silica (2 wt. % protective coating, relative to the weight of the pellets with the polyvinyl acetate coating). The cumulative release (%), plotted versus time, is shown. The curves show the release from the pellets themselves and from tablets that were produced in various conditions. Measurement series A relates to tablets that were produced with a compression pressure of 141 MPa and have a hardness of 80 N and a disintegration time of less than 1 minute. Measurement series B relates to tablets that were produced with a compression pressure of 168 MPa and have a hardness of 125 N and a disintegration time of 1 to 2 minutes. Measurement series C relates to tablets that were produced with a compression pressure of 221 MPa and have a hardness of 170 N and a disintegration time of 3 to 4 minutes.

First, pellets were produced with the active substance ADD 006, as was described in production examples 1 and 2. These pellets were then coated to control release. A polyvinyl acetate dispersion containing talc (10 wt. %) and triethyl citrate (10 wt. %) was used for this. The pellets were provided with an amount of 40 wt. % of coating dispersion, the percentage by weight being found from the solids content of the coating (polyvinyl acetate, talc and triethyl citrate), relative to the weight of the pellet cores. The pellets were then provided with 2 wt. % of a coating of hydroxypropyl methylcellulose and colloidal silica, the last-mentioned percentage by weight being calculated from the weight of the solid ingredients of the protective coating, relative to the weight of the pellets with the polyvinyl acetate coating. The release behavior of these pellets is shown in FIG. 3.

In addition, tablets were produced from the pellets. The release behavior of the tablets was also investigated, as described in example 1, and is shown in FIG. 3.

Example 4

The example relates to investigation of the release behavior of products according to the invention. In particular the example elucidates the effect of tableting on the release behavior.

Figure 4:
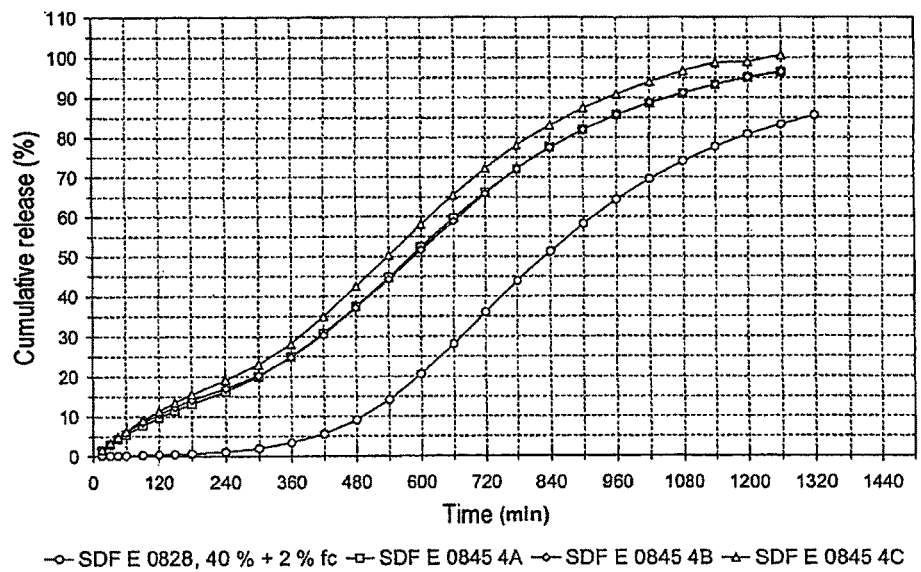
FIG. 4 shows the influence of the compression force on the release of the active substance from tablets with a diameter of 12 mm and a weight of 884.2 mg, containing 200 mg ADD 006. The tablets were produced in each case using pellets that have a pellet core with the active substance ADD 006. The pellet core was coated with 40 wt. % of a coating consisting, relative to the weight of the pellet cores, of polyvinyl acetate, triethyl citrate (7.5 wt. %, relative to the weight of the polyvinyl acetate) and talc (10 wt. %, relative to the weight of the polyvinyl acetate) and a protective coating of hydroxypropyl methylcellulose and colloidal silica (2 wt. % protective coating, relative to the weight of the pellets with the polyvinyl acetate coating). The cumulative release (%), plotted versus time, is shown. The curves show the release from the pellets themselves and from tablets that were produced in various conditions.

First, pellets were produced with the active substance ADD 006, as was described in production examples 1 and 2. These pellets were then coated to control release. A polyvinyl acetate dispersion containing talc (10 wt. %) and triethyl citrate (7.5 wt. %) was used for this. The pellets were provided with an amount of 40 wt. % of coating dispersion, the percentage by weight being found from the solids content of the coating (polyvinyl acetate, talc and triethyl citrate), relative to the weight of the pellet cores. The pellets were then provided with 2 wt. % of a coating of hydroxypropyl methylcellulose and colloidal silica, the last-mentioned percentage by weight being calculated from the weight of the solid ingredients of the protective coating, relative to the weight of the pellets with the polyvinyl acetate coating. The release behavior of these pellets is shown in FIG. 4.

In addition, tablets were produced from the pellets. The release behavior of the tablets was also investigated, as described in example 1, and is shown in FIG. 4.

Test Examples

The following examples relate to investigation of pellet cores for determining the surface roughness.

Test Example 1

Pellets with the batch designation SFD E 0724 were investigated. An electron micrograph of pellets of this kind is shown in FIG. 6. A segment from the surface of a pellet from this batch was scanned with a laser profilometer, as described previously. A graphical representation of the measurement results is shown in FIG. 7 A as a surface graph and in FIG. 7 B as a contour diagram. The roughness was calculated using a reduced data set, as described previously. A surface graph based on the reduced data set is shown in FIG. 7 C, and the corresponding contour diagram is shown in FIG. 7 D.

Using the method of least squares, a sphere was determined that provides an optimum representation of the measurement points of the reduced set. The coordinates of the center of this sphere were determined as 385 µm; 324 µm and −293 µm. The optimum radius R was 516 µm. The distribution of the data after adjustment is shown in FIG. 7 E. In this diagram the horizontal axis denotes the measured data points. The vertical axis denotes the distance of the measured points of the profile from the surface of the ideal sphere with the coordinates of the center and the radius as stated previously. The data points are distributed uniformly above and below the horizontal axis.

Statistical analysis of the data shows that the mean roughness $\sigma_d$ has a value of 13.6 µm and that the relative mean roughness $\sigma_d/R$ has a value of 2.64%. The absolute roughness has a value of more than 50 µm. The pellet core investigated therefore does not fulfill the criteria according to the invention for a pellet core with a smooth surface.

Test Example 2

Another pellet from the same batch already mentioned in test example 1 was investigated in the same way as described previously. A graphical representation of the measurement results is shown in FIG. 8 A as a surface graph and in FIG. 8 B as a contour diagram. The reduced data set that was used for calculating the roughness forms the basis of the surface graph shown in FIG. 8 C, and of the contour diagram shown in FIG. 8 D.

Using the method of least squares, a sphere was determined that provides an optimum representation of the measurement points of the reduced set. The coordinates of the center of this sphere were determined as 434 µm; 336 µm and −841 µm. The optimum radius R was 983 µm. The distribution of the data after adjustment is shown in FIG. 8 E. Statistical analysis of the data shows that the mean roughness $\sigma_d$ has a value of 15.9 µm and the relative mean roughness $\sigma_d/R$ has a value of 1.62%. The absolute roughness has a value of more than 50 µm. The pellet core investigated therefore does not fulfill the criteria according to the invention for a pellet core with a smooth surface.

Test Example 3

Pellets with the batch designation SFD E 0718 were investigated. An electron micrograph of pellets of this kind is shown in FIG. 9. A segment from the surface of a pellet from this batch was scanned with a laser profilometer, as described previously. A graphical representation of the measurement results is shown in FIG. 10 A as a surface graph and in FIG. 10 B as a contour diagram. The roughness was calculated using a reduced data set, as described previously. A surface graph based on the reduced data set is shown in FIG. 10 C, and the corresponding contour diagram is shown in FIG. 10 D.

Using the method of least squares, a sphere was determined that provides an optimum representation of the measurement points of the reduced set. The coordinates of the center of this sphere were determined as 391 µm; 337 µm and −680 µm. The optimum radius R was 713 µm. The distribution of the data after adjustment is shown in FIG. 10 E. Statistical analysis of the data shows that the mean roughness $\sigma_d$ has a value of 10.7 µm and the relative mean roughness $\sigma_d/R$ has a value of 1.5%. The absolute roughness has a value of about 50 µm. The pellet core investigated therefore does not fulfill the criteria according to the invention for a pellet core with a smooth surface.

Test Example 4

Figure 11A:
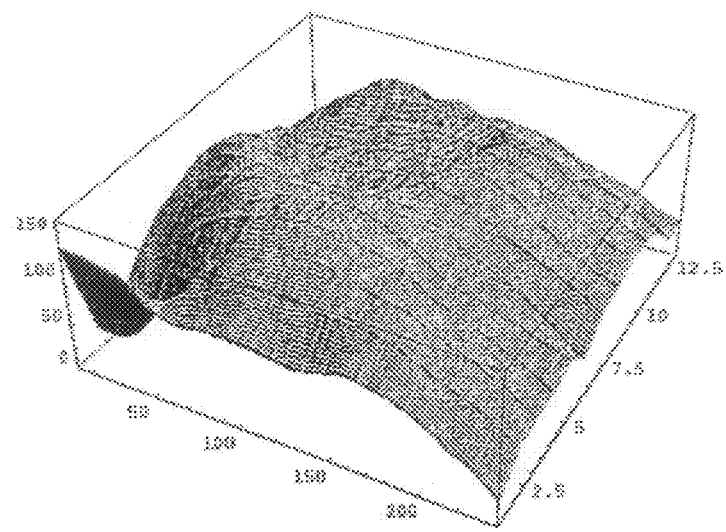
Figure 11B:
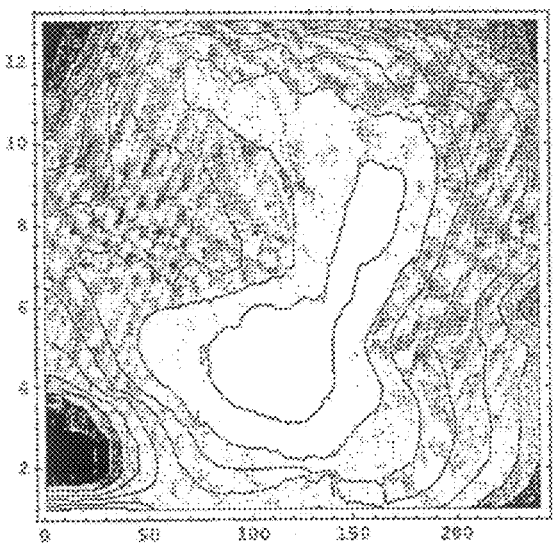
Figure 11C:
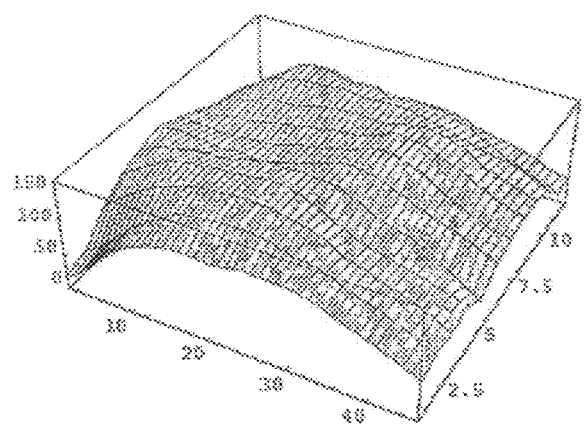
Figure 11D:
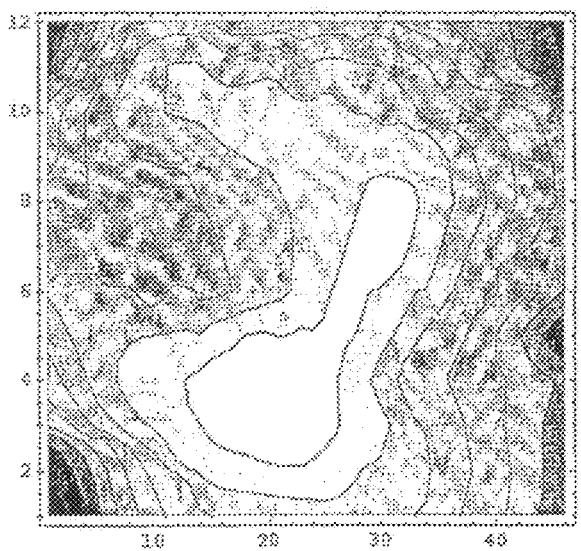

Another pellet from the same batch already mentioned in test example 3 was investigated in the same way as described previously. A graphical representation of the measurement results is shown in FIG. 11A as a surface graph and in FIG. 11B as a contour diagram. The reduced data set that was used for calculating the roughness forms the basis of the surface graph shown in FIG. 11C, and of the contour diagram shown in FIG. 11D.

Figure 11E:
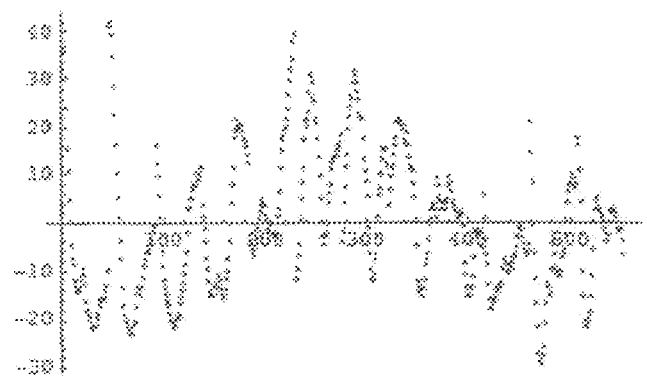

Using the method of least squares, a sphere was determined that provides an optimum representation of the measurement points of the reduced set. The coordinates of the center of this sphere were determined as 309 µm; 297 µm and −656 µm. The optimum radius R was 804 µm. The distribution of the data after adjustment is shown in FIG. 11E. Statistical analysis of the data shows that the mean roughness $\sigma_d$ has a value of 14.31 µm and the relative mean roughness $\sigma_d/R$ has a value of 1.78%. The absolute roughness has a value of 45 µm. The pellet core investigated therefore does not fulfill the criteria according to the invention for a pellet core with a smooth surface.

Test Example 5

Pellets with the batch designation SFD E 0572 were investigated. An electron micrograph of pellets of this kind is shown in FIG. 12. A segment from the surface of a pellet from this batch was scanned with a laser profilometer, as described previously. A graphical representation of the measurement results is shown in FIG. 13 A as a surface graph and in FIG. 13 B as a contour diagram. The roughness was calculated using a reduced data set, as described previously. A surface graph based on the reduced data set is shown in FIG. 13 C, and the corresponding contour diagram is shown in FIG. 13 D.

Using the method of least squares, a sphere was determined that provides an optimum representation of the measurement points of the reduced set. The coordinates of the center of this sphere were determined as 349 µm; 315 µm and −369 µm. The optimum radius R was 595 µm. The distribution of the data after adjustment is shown in FIG. 13 E. Statistical analysis of the data shows that the mean roughness $\sigma_d$ has a value of 5.5 µm and the relative mean roughness $\sigma_d/R$ has a value of 0.92%. The absolute roughness has a value of 17 µm. The pellet core investigated therefore fulfills the criteria according to the invention for a pellet core with a smooth surface.

Test Example 6

Pellets with the batch designation SFD E 0614 were investigated. An electron micrograph of pellets of this kind is shown in FIG. 14. A segment from the surface of a pellet from this batch was scanned with a laser profilometer, as described previously. A graphical representation of the measurement results is shown in FIG. 15 A as a surface graph and in FIG. 15 B as a contour diagram. The roughness was calculated using a reduced data set, as described previously. A surface graph based on the reduced data set is shown in FIG. 15 C, and the corresponding contour diagram is shown in FIG. 15 D.

Using the method of least squares, a sphere was determined that provides an optimum representation of the measurement points of the reduced set. The coordinates of the center of this sphere were determined as 293 µm; 919 µm and −358 µm. The optimum radius R was 677 µm. The distribution of the data after adjustment is shown in FIG. 15 E. Statistical analysis of the data shows that the mean roughness $\sigma_d$ has a value of 7.1 µm and the relative mean roughness $\sigma_d/R$ has a value of 1.06%. The absolute roughness has a value of 19 µm. The pellet core investigated therefore fulfills the criteria according to the invention for a pellet core with a smooth surface.

Test Example 7

Another pellet from the same batch already mentioned in test example 6 was investigated in the same way as described previously. A graphical representation of the measurement results is shown in FIG. 16 A as a surface graph and in FIG. 16 B as a contour diagram. The reduced data set that was used for calculating the roughness forms the basis of the surface graph shown in FIG. 16 C, and of the contour diagram shown in FIG. 16 D.

Using the method of least squares, a sphere was determined that provides an optimum representation of the measurement points of the reduced set. The coordinates of the center of this sphere were determined as 272 µm; 200 µm and −491 µm. The optimum radius R was 652 µm. The distribution of the data after adjustment is shown in FIG. 16 E. Statistical analysis of the data shows that the mean roughness $\sigma_d$ has a value of 8.2 µm and the relative mean roughness $\sigma_d/R$ has a value of 1.26%. The absolute roughness has a value of 30 µm. The pellet core investigated therefore fulfills the criteria according to the invention for a pellet core with a smooth surface.

The invention claimed is:

1. A pharmaceutical pellet, comprising:
   (a) a spherical core with a smooth surface, wherein the spherical core is homogeneous and comprises an active substance; and
   (b) a coating, on the core, which controls pH-independent release of the active substance, and which does not comprise the active substance;
   wherein the core has a diameter in the range of from 0.2 to 2.0 mm;
   wherein the surface of the core has a mean roughness of less than 10 µm and a relative mean roughness of less than 2%;
   wherein the active substance is uniformly distributed in the core; and
   wherein said pellet additionally has an outer protective coating which comprises a water-soluble film-forming agent.

2. The pellet as claimed in claim 1;
   wherein the core has a length-width ratio of less than about 1.4.

3. The pellet as claimed in claim 1;
   wherein the core has a diameter in the range from 0.2 to 1.6 mm.

4. The pellet as claimed in claim 1;
   wherein the surface of the core has a mean roughness of less than 7 µm.

5. The pellet as claimed in claim 1;
   wherein the coating comprises at least one polymer, which is selected from ammonium methacrylate copolymer, cellulose acetate butyrate, cellulose acetate, cellulose acetate propionate, ethyl cellulose, poly(ethylacrylate-methylacrylate), and polyvinyl acetate.

6. The pellet as claimed in claim 1;
   wherein the core further comprises a carrier and/or a binder.

7. The pellet as claimed in claim 1;
   wherein the active substance is a water-soluble active substance or a water soluble salt of a sparingly soluble active substance.

8. The pellet as claimed in claim 1;
   wherein the release of the active substance follows a profile with a lag phase from 60 minutes to 840 minutes; and
   wherein, during the lag phase, a proportion of 5 wt. % or less of the active substance is released.

9. The pellet as claimed in claim 1;
   wherein the active substance is released from the pellet with a profile such that, after a lag phase, the release of the active substance is between 3 and 25 wt. % per hour.

10. A collection of pellets,
    wherein at least 90% of the pellets correspond to the definition according to claim 1.

11. The collection as claimed in claim 10;
    wherein the pellets have a particle size distribution such that 90% of the pellets have a diameter that differs from the mean diameter by not more than half the mean diameter.

12. A collection of cores;
    wherein at least 90% of the cores:
    (i) are homogeneous;
    (ii) comprise an active substance that is uniformly distributed in each core;
    (iii) have a diameter in the range of from 0.2 to 2.0 mm;
    (iv) have a smooth surface with a mean roughness of less than 10 µm and a relative mean roughness of less than 2%; and
    (v) have a length-width ratio of less than about 1.4.

13. The pellet as claimed in claim 1;
    wherein the core has a length-width ratio of less than about 1.3.

14. The pellet as claimed in claim 1;
    wherein the core has a length-width ratio of less than about 1.2.

15. The pellet as claimed in claim 1;
    wherein the core has a length-width ratio of less than about 1.05.

16. The pellet as claimed in claim 1;
    wherein the release of the active substance follows a profile with a lag phase of from 60 minutes to 540 minutes; and
    wherein, during the lag phase, a proportion of 5 wt. % or less of the active substance is released.

17. The pellet as claimed in claim 1;
    wherein the active substance is released from the pellet with a profile such that, after a lag phase, the release of the active substance is between 3 and 15 wt. % per hour.

18. The pellet as claimed in claim 1;
    wherein the active substance is released from the pellet with a profile such that, after a lag phase, the release of the active substance is between 3 and 6.5 wt. % per hour.

19. The pellet as claimed in claim 1;
    wherein the core has a diameter in a range of from 0.4 to 1.6 mm.

20. The pellet as claimed in claim 1;
    wherein the core has a diameter in a range of from 0.4 to 1.4 mm.

21. A pharmaceutical pellet, comprising:
    (a) a spherical core with a smooth surface, wherein the spherical core is homogeneous and comprises an active substance;
    (b) a coating, on the core, which controls pH-independent release of the active substance, and which does not comprise the active substance;
    wherein the core has a diameter in the range of from 0.2 to 2.0 mm;
    wherein the surface of the core has a mean roughness of less than 10 µm and a relative mean roughness of less than 2%; and wherein the active substance is uniformly distributed in the core; and (c) an interlayer, which comprises a water-soluble film forming agent, provided between the core comprising the active substance and the coating that controls the release of the active substance.

22. A method for producing a pellet as claimed in claim 1;

wherein the method comprises the following stages:

(a) preparing a pellet core which comprises the active substance, and which has:

a length width ratio of less than about 1.4; and a mean roughness of less than 10 µm; and (b) spraying, onto the pellet core, an aqueous or organic solution or dispersion comprising a film forming agent that controls the pH independent release of the active substance.

23. A method for producing a tablet, comprising the following stages:

(a) mixing pellets as claimed in claim 1 with one or more ingredients, selected from fillers, binders, disintegrants, flow regulators, and lubricants, to form a mixture; and (b) compressing the mixture to form a tablet.

24. The method as claimed in claim 23;

wherein, during the compression stage, some of the pellets are disrupted, so that the release of the active substance from the tablet does not exhibit a lag phase.

25. The pellet as claimed in claim 1;

wherein the water-soluble film-forming agent is hydroxypropyl methylcellulose.

26. The method as claimed in claim 22;

wherein the pellet core is prepared so as to have a relative mean roughness of less than 2%.

27. The pellet as claimed in claim 21;

wherein the water-soluble film forming agent of the interlayer is hydroxypropyl methylcellulose.

* * * * *